(12) United States Patent
Ostrer et al.

(10) Patent No.: US 12,331,345 B2
(45) Date of Patent: *Jun. 17, 2025

(54) METHODS AND COMPOSITIONS FOR DIAGNOSING AND TREATING, GERMLINE MISMATCH REPAIR DEFICIENCIES, LYNCH SYNDROME AND ASSESSING GERMLINE RISKS OF CANCER

(71) Applicants: MORGAN AND MENDEL GENOMICS, INC., New York, NY (US); ALBERT EINSTEIN COLLEGE OF MEDICINE, Bronx, NY (US)

(72) Inventors: Harry Ostrer, New York, NY (US); Johnny C. Loke, Valley Cottage, NY (US); Ishraq Alim, New York, NY (US)

(*) Notice: Subject to any disclaimer, the term of this patent is extended or adjusted under 35 U.S.C. 154(b) by 108 days.

This patent is subject to a terminal disclaimer.

(21) Appl. No.: 17/674,400

(22) Filed: Feb. 17, 2022

(65) Prior Publication Data

US 2022/0260553 A1    Aug. 18, 2022

Related U.S. Application Data

(60) Provisional application No. 63/233,064, filed on Aug. 13, 2021, provisional application No. 63/150,347, filed on Feb. 17, 2021.

(51) Int. Cl.
| | | |
|---|---|---|
| G01N 31/00 | (2006.01) | |
| C12Q 1/6804 | (2018.01) | |
| C12Q 1/6827 | (2018.01) | |
| G01N 15/14 | (2006.01) | |
| G01N 33/50 | (2006.01) | |
| G01N 33/53 | (2006.01) | |
| G01N 33/574 | (2006.01) | |
| G01N 15/10 | (2006.01) | |

(52) U.S. Cl.
CPC ......... *C12Q 1/6827* (2013.01); *C12Q 1/6804* (2013.01); *G01N 15/14* (2013.01); *G01N 33/5023* (2013.01); *G01N 33/5035* (2013.01); *G01N 33/5041* (2013.01); *G01N 33/57419* (2013.01); *G01N 33/57484* (2013.01); *G01N 2015/1006* (2013.01)

(58) Field of Classification Search
None
See application file for complete search history.

(56) References Cited

U.S. PATENT DOCUMENTS

| | | | |
|---|---|---|---|
| 4,444,879 A * | 4/1984 | Foster ................ | G01N 33/6854 435/805 |
| 7,572,640 B2 | 8/2009 | Goix et al. | |
| 7,838,250 B1 | 11/2010 | Goix et al. | |
| 10,718,774 B2 | 7/2020 | Ostrer et al. | |
| 11,981,959 B2 * | 5/2024 | Ostrer ................ | G01N 33/5041 |
| 2002/0164659 A1 | 11/2002 | Rao et al. | |
| 2007/0166835 A1 | 7/2007 | Bobrow et al. | |
| 2008/0206757 A1 | 8/2008 | Lin et al. | |
| 2014/0194315 A1 | 1/2014 | Cesano et al. | |
| 2017/0299600 A1 | 10/2017 | Ostrer et al. | |
| 2018/0074049 A1 | 3/2018 | Loke et al. | |
| 2020/0309781 A1 | 10/2020 | Ostrer et al. | |

FOREIGN PATENT DOCUMENTS

| | | | |
|---|---|---|---|
| EP | 3 670 673 | 6/2020 | |
| WO | WO 2013/004618 | 1/2013 | |
| WO | WO 2016/028870 | 2/2016 | |
| WO | WO-2016028870 A1 * | 2/2016 | ........... C12Q 1/6886 |
| WO | WO 2018/091419 | 5/2018 | |

OTHER PUBLICATIONS

Drost et al. (Genetics in Medicine (2019) 21:1486-1496; https://dot.org/ 10, 1038/s41436-018-0372-2) (Year: 2019).*
Adar et al. (Gastroenterology (May 2018), vol. 154, No. 6, Supp. 1, p. S-791) (Year: 2018).*
Hollenbach et al. (PLOSone, 2011 6/7, e21808). (Year: 2011).*
Arora et al. Cancer Res. (2016) 76 (14 Supplement) 5286 Abstract (Year: 2016).*
Becker A.A. et al., "A 24-Color Metaphase-Based Radiation Assay Discriminates Heterozygous BRCA2 Mutation Carriers from Controls by Chromosomal Radiosensitivity", Breast Cancer Res Treat 135:167-175 (2012).
Bogdanova N. et al., "Nigmegen Breakage Syndrome Mutations and Risk of Breast Cancer", Int. J. Cancer 122:802-806 (2008).
Bouwman P. et al., "A High-Throughput Functional Complementation Assay for Classification of BRCA1 Missense Variants", Cancer Discovery 3:1142-1155 (Oct. 2013).

(Continued)

*Primary Examiner* — Lisa V Cook
(74) *Attorney, Agent, or Firm* — McDonnell Boehnen Hulbert & Berghoff LLP

(57) ABSTRACT

Heritable pathogenic variants in the mismatch repair (MMR) pathway, also known as Lynch Syndrome (LS), can lead to the development of colon cancer and other cancers. Following mismatch, a complex of proteins consisting of MLH1, MSH2, MSH6 and PMS2 translocate into the nucleus to signal recruitment of repair mechanisms. Flow cytometry-based, functional variant assays (FVAs), were developed to determine whether variants in these MMR repair genes and/or other related genes would augment the nuclear translocation of MLH1 and MSH2 and downstream nuclear phosphorylation of ATM and ATR in response to DNA mismatches. Each assay distinguished pathogenic variants in MMR repair genes (MLH1, MSH2, PMS2 and MSH6) from benign controls. The combination of multiple assays provided robust separation between heterozygous pathogenic variant carriers and benign controls. The ability to produce distinct molecular phenotypes by these assays suggest FVA assays of MMR pathways could be used to identify LS and associated risk of colon and other cancers and could act as an adjunct to MMR gene sequencing panels in categorizing variants.

6 Claims, 22 Drawing Sheets

(56) References Cited

OTHER PUBLICATIONS

Carvalho M.A. et al., "Determination of Cancer Risk Associated With Germ Line BRCA1 Missense Variants by Functional Analysis", Cancer Research 67(4):1494-1501 (Feb. 15, 2007).
Carvalho M.A. et al., "Functional Assays for BRCA1 and BRCA2", Int J Biochem Cell Biol. 39(2):298-310 (2007).
Casadei S. et al., "Contribution of Inherited Mutations in the BRCA2-Interacting Protein PALB2 to Familial Breast cancer", Cancer Research 71(6):2222-2229 (Mar. 15, 2011).
Castilla L.H. et al., "Mutations in the BRCA1 Gene in Families With Early-Onset Breast and Ovarian Cancer", Nature Genetics 8:387-391 (Dec. 1994).
Chang S. et al., "Tumor Suppressor BRCA1 Epigenetically Controls Oncogenic MicroRNA-155", Nature Medicine 17(10):1275-1282 (Oct. 2011).
Chen J. et al., "Stable Interaction Between the Products of the BRCA1 and BRCA2 Tumor Suppressor Genes in Mitotic and Meiotic Cells", Molecular Cell 2:317-328 (Sep. 1998).
De Jager et al., (Clin Vaccine Immunol Jan. 2003 vol. 10 No. 1: 133-139).
Desjardins S. et al., "Variations in the NBN/NBSI Gene and the Risk of Breast Cancer in Non-BRCAI/2 French Canadian Families With High Risk of Breast Cancer", BMC Cancer 9:181 (Jun. 2009).
Drost et al. "A functional assay-based procedure to classify mismatch repair gene variants in Lynch syndrome" Genetics in Medicine 21(7):1486-1496 (Jul. 2019).
Drost et al. "Two integrated and highly predictive functional analysis-based procedures for the classification of MSH6 variants in Lynch syndrome" Genetics in Medicine 22(5):847-856 (May 2020).
Febrer E. et al., "Mitotic Delay in Lymphocytes from BRCA1 Heterozygotes Unable to Reduce the Radiation-Induced Chromosomal Damage", DNA Repair 7:1907-1911 (2008).
Friedman L.S. et al., "Confirmation of BRCA1 by Analysis of Germline Mutations Linked to Breast and Ovarian cancer in Ten Families", Nature Genetics 8:399-404 (Dec. 1994).
Gorski B. et al., "Founder Mutations in the BRCA1 Gene in Polish Families With Breast-Ovarian Cancer", Am. J. Hum. Genet. 66:1963-1968 (2000).
Gowen L.C. et al., "Brca1 Deficiency Results in Early Embryonic Lethality Characterized by Neuroepithelial Abnormalities", Nature Genetics 12:191-194 (Feb. 1996).
Griwatz et al. (Journal of Immunological Methods 183.2 (1995): 251-265) (Year: 1995).
Hakem R. et al., "The Tumor Suppressor Gene Brca1 is Required for Embryonic Cellular Proliferation in the Mouse", Cell 85:1009-1023 (Jun. 28, 1996).
Heikkinen K et al., "RAD50 and NBS1 are Breast Cancer Susceptibility Genes Associated With Genomic Instability", Carcinogenesis 27(8):1593-1599 (2006).
Heinen "Mismatch repair defects and Lynch syndrome: the role fo the basic scientist in the battle against cancers" DNA Repair (Amst). Feb. 2016;38:127-134. doi: 10.1016/j.dnarep.2015.11.025. Epub Dec. 2, 2015.
Hsu H-M et al., "Breast Cancer Risk is Associated With the Genes Encoding the DNA Double-Strand Break Repair Mre11/Rad50/Nbs1 Complex", Cancer Epidemiol Biomarkers Prey 16(10):2024-2032 (2007).
Huen et al. "BRCA1 and its toolbox for the maintenance of genome integrity." Nat. Rev. Mol. Cell Biol. 11(2):138-48 (Feb. 2010).
Jara L. et al., "Molecular Analysis of the Eighteen Most Frequent Mutations in the BRCA1 Gene in 63 Chilean Breast Cancer Families", Biol Res 37:469-481 (2004).
Keimling M. et al., "The power of DNA double-strand break (DSB) repair testing to predict breast cancer susceptibility", The FASEB Journal, (2012), vol. 26, No. 5, pp. 2094-2104.
Kim et al., (Lab Chip, 2005, 5, 657-664).
Lee M.S. et al., "Comprehensive Analysis of Missense Variations in the BRCT Domain of BRCA1 by Structural and Functional Assays", Cancer Research 70(12):4880-4890 (Jun. 15, 2010).

Liu "Interactions of human mismatch repair proteins MutSa and MutLa with proteins of the ATR-Chk1 pathway" Journal of Biol. Chem Feb. 19, 2010;285(8):5974-82. doi: 10.1074/jbc.M109.076109. Epub Dec. 22, 2009.
Loke J. et al., "Rapidly Screening Variants of Uncertain Significance in the MAP3K1 Gene for Phenotypic Effects", Clinical Genetics 81:272-277 (2012).
Loke et al., "Mutations in MAP3K1 tilt the balance from SOX9/FGF9 to WNT/Beta-catenin signaling" Human Molecular Genetics, 2013, 1-11.
Mannucci A. et al., "Biomass Accumulation Modelling in a Highly Loaded Biotrickling Filter for Hydrogen Sulphide Removal", Chemosphere 88:712-717 (2012).
Murray M.L. et al., "Follow-Up of Carriers of BRCA1 and BRCA2 Variants of Unknown Significance, Variant Reclassification and Surgical Decisions", Genetics in Medicine 13(12):998-1005 (Dec. 2011).
Quail et al., (Nature Methods 5.12 (2008): 1005). (Year: 2008) and supplement.
Schmidt et al. (Methods 48.3 (2009): 240-248).
Scully R. et al., "Association of BRCA1 With Rad51 in Mitotic and Meiotic Cells", Cell 88:265-275 (Jan. 24, 1997).
Seal S. et al., "Truncating Mutations in the Fanconi Anemia J Gene BRIP1 are Low-Penetrance Breast Cancer Susceptibility Alleles", Nature Genetics 38(11):1239-1241 (Nov. 2006).
Serova O. et al., "A High Incidence of BRCA1 Mutations in 20 Breast-Ovarian Cancer Families", Am. J. Hum. Genet. 58:42-51 (1996).
Stacey S.N. et al., "The BARD1 Cys557Ser Variant and Breast Cancer Risk in Iceland", PLoS Medicine 3(7):1103-1113 (Jul. 2006).
Starita L.M. et al., "Substrates of the BRCA1-Dependent Ubiquitin Ligase", Cancer Biology & Therapy 5(2):137-141 (Feb. 2006).
Struewing J.P. et al., "Detection of Eight BRCAI Mutations in 10 Breast/Ovarian Cancer Families, Including I Family With Male Breast Cancer", Am. J. Hum. Genet. 57:1-7 (1995).
Struewing J.P. et al., "The Carrier Frequency of the BRCA1 185delAG Mutation is Approximately 1 Percent in Ashkenazi Jewish Individuals", Nature Genetics 11:198-200 (Oct. 1995).
Syeda M.M. et al., "Prediction of breast cancer risk based on flow-variant analysis of circulating peripheral blood B cells", Genetics in Medicine, (2017), 7 pages doi:10.1038/gim.2016.222.
Thompson et al. "A Multifactorial Likelihood Model for MMR Gene Variant Classification Incorporating Probabilities Based on Sequence Bioinformatics and Tumor Characteristics: A Report from the Colon Cancer Family Registry" Human Mutation 34(1):200-209 (2012).
Tonin P. et al., "Frequency of Recurrent BRCA1 and BRCA2 Mutations in Ashkenazi Jewish Breast Cancer Families", Nature Medicine 2(11):1179-1183 (Nov. 1996).
Trenz K. et al., "Mutagen Sensitivity of Peripheral Blood from Women Carrying a BRCA1 or BRCA2 Mutation", Mutation Research 500:89-96 (2002).
Valle et al., "Genetic predisposition to colorectal cancer: syndromes, genes, classification of genetic variants and Implications for precision medicine" J Pathol 247:574-588 (Feb. 2019).
Venkitaraman A.R., "Cancer Suppression by the Chromosome Custodians, BRCA1 and BRCA2", Science 343:1470-1475 (Mar. 28, 2014).
Venkitaraman A.R., "Linking the Cellular Functions of BRCA Genes to Cancer Pathogenesis and Treatment", Annu. Rev. Pathol. Mech. Dis. 4:461-487 (2009).
Vilasova Z. et al, "Changes in Phosphorylation of Histone H2A.X and p53 in Response of Peripheral Blood Lymphocytes to Gamma Irradiation", Acta Biochimica Polonica 55(2):381-390 (2008).
Wang Y. et al., "BASC, a Super Complex of BRCA1-Associated Proteins Involved in the Recognition and Repair of Aberrant DNA Structures", Genes and Development 14:927-939 (2000).
Wilson et al. (ACS Nano 1.5 (2007): 487-493).
The International Search Report for International Application No. PCT/US2022/016758; mailed Jul. 1, 2022, pp. 1-4.
Boland et al. (Fam Cancer, 2008: 7(1)41-52, Published Online Jul. 17, 2007 (Year: 2008).

(56) References Cited

OTHER PUBLICATIONS

Engel et al., (Clin Gastroenterol. Heptol. Feb. 2010 8(2): 174-182 (Year: 2010).
Yurgelin et al. (Advances in Lynch Syndrome, 2018, pp. 101-109, asco.org/edbook) (Year: 2018).
Christmann et al., "Nuclear Translocation of Mismatch Repair Proteins MSH2 and MSH6 as a Response of Cells to Akylating Agents" The Journal of Biological Chemistry, 275(46):36256-62 (Nov. 2000).
Cejka et al., "Methylation-induced G2/M arrest requires a full complement of the mismatch repair protein hMHL1" The EMBO Journal, 22(9):2245-54 (May 2003).
Molaei et la., "Colorectal cancer in Iran: immunohistochemical profiles of four mismatch repair proteins" International Journal of Colorectal Disease, 25:63-69 (Aug. 2009).
Supplementary European Search Report for EP 22 75 6908; pp. 1-3, mailed Jan. 7, 2025.

\* cited by examiner

METHODS AND COMPOSITIONS FOR DIAGNOSING AND TREATING, GERMLINE MISMATCH REPAIR DEFICIENCIES, LYNCH SYNDROME AND ASSESSING GERMLINE RISKS OF CANCER

CROSS REFERENCE TO RELATED APPLICATIONS

This application claims priority to U.S. Provisional Application No. 63/150,347, filed Feb. 17, 2021, and to U.S. Provisional Application No. 63/233,064, filed Aug. 13, 2021, the disclosure of which is incorporated by reference in its entirety.

STATEMENT REGARDING FEDERALLY SPONSORED RESEARCH

This invention was made with government support under CA232867 awarded by the National Institutes of Health. The government has certain rights in the invention.

FIELD OF THE DISCLOSURE

This disclosure relates to methods and composition for diagnosing LS and assessing germline risk of cancer (e.g., colon cancer) based on analysis of nuclear and cytoplasmic proteins in cells (patient derived or transformed cell lines) that are part of the DNA mismatch repair (MMR) pathway.

BACKGROUND

Lynch syndrome: Lynch syndrome (LS), also known as hereditary non-polyposis colorectal cancer (HNPCC) is the most common form of hereditary colon cancer. It occurs due to defects in the MMR pathway. Predisposition is caused by autosomal dominant heterozygous germline pathogenic variants in one of five MMR genes: mutL homologue 1 (MLH1), mutS homologue 2 (MSH2), mutS homologue 6 (MSH6), postmeiotic segregation increased 2 (PMS2), or Epithelial Cell Adhesion Molecule (EPCAM). Risk of LS is identified in the clinic by the Amsterdam II criteria (Vasen et al., *Gastroenterology*, 116(6) 1453-6 (1999)) and the revised Bethesda guidelines (Umar et al., *J Natl Cancer Inst.*, 96(4) 261-268 (2004)). The Amsterdam II criteria requires at least three relatives with LS associated cancers (colorectal, endometrium, stomach, ovary, ureter, renal pelvis, brain, small bowel, hepatobiliary tract or skin cancer) that are also: one first-degree relative, two successive affected generations, one diagnosis <50 years of age, familial adenomatous polyposis (FAP) excluded, and tumors verified by pathology when possible (Vasen et al., *Gastroenterology*, 116(6) 1453-6 (1999)). The Bethesda criteria adds to this by providing criteria to justify microsatellite instability (MSI) testing. These criteria are: colorectal cancer (CRC) patient <50 years old, presence of synchronous or metachronous colorectal or other LS-associated tumors (regardless of age), MSI-High (MSI-H) histology in patients <60 years old, LS-associated tumor diagnosed in one first-degree relative <50 years old, and LS-associated tumor diagnosed at any age in two first- or second-degree relative (Umar et al., *J Natl Cancer Inst.*, 96(4)261-268 (2004)). The Bethesda criteria is limited to diagnosis only after tumors have developed, as MSI is measured in the tumor tissue. Individuals who do not fit the Amsterdam or Bethesda criteria may nonetheless have germline defects in the MMR pathway that put them at increased risk for developing cancer.

Cancers associated with LS: Between 2-5% of all colon cancers are defined as hereditary. The majority of hereditary colon cancers are categorized as LS (>80%); other rare causes results from pathogenic variants in other pathways. Those identified with pathogenic MMR gene variants and meet the Amsterdam II criteria have a lifetime risk of 50-80% of developing colorectal cancer (Stoffel et al., *Gastroenterology*, 137(5):1621-7(2009)). LS affected individuals develop colonic adenomas and very rarely polyposis. In addition to CRC, individuals with LS can form other cancers, including endometrial cancer (40-60% lifetime risk), stomach (11-19% lifetime risk), ovary (9-12% lifetime risk), hepatobiliary tract (2-7% lifetime risk), upper urinary tract (4-5% lifetime risk), pancreatic (3-4%), small bowel (1-4%) and glioblastoma (1-3%) (Jasperson et al., *Gastroenterology*, 138(6) 2044-58, (2010)). Specific cancers due to LS can arise from pathogenic variants in specific genes. Pathogenic variants in MLH1 cause predominantly CRC; variants in MSH2 cause predominantly endometrial cancer; variants in MSH6 cause predominantly stomach cancer; variants in PMS2 cause predominantly ovary cancer and variants in EPCAM cause predominantly hepatobiliary tract, upper urinary tract, pancreatic, small bowel and/or CNS cancers.

MMR pathway: MMR is the mechanism of recognizing and repairing erroneous insertion, deletion misincorporation of bases that leads to mismatched base pairs in otherwise complementary sequences. LS is caused by pathogenic variants in MMR repair genes, with specific focus in the clinical setting to MLH1 MSH2, MSH6 and PMS2 (FIG. 1). During MMR these proteins form heterodimers, MutSα (containing MSH2 and MSH6) and MutLβ (containing MLH1 and PMS2), and are transported into the nucleus to the site of mismatch and cause repair by homologous recombination and/or signal for cell death (Mirzoeva et al., *Mol Cancer Ther.*, 5:2757-66 (2006); Eich et al., *Mol Pharmacol.*, 78:943-51 (2010)). Studies using loss of function pathogenic variants in MMR genes in cell lines show that the remaining machinery in the MMR pathway continue to cycle inside the nucleus as a frustrated response to the repair (Mojas et al., *Genes & Development*, 21:3342-55 (2008); Ochs & Kaina, *Cancer Research*, 60, 5815-24 (2000); Fu et al., *Nat Rev Cancer*, 12(2) 104-120 (2012)).

Mismatches can result from environmental stresses including UV, radiation, radiomimetic agents and hypoxia. They can also be artificially induced by alkylating agents such as methylnitronitrosoguanidine (MNNG) and Diazald®. MNNG and Diazald® form O4-methylguanine adducts resulting in mismatch repair. Nuclear extracts show increased expression of MUTSα and MUTLβ complexes in HeLa cell lines treated with MNNG. MNNG treatment also increases ATR kinase activity and phosphorylation of CHK1 in whole cell, both of which are downstream signals of MMR pathway (Yoshioka et al., *Mol Cell*, 19; 22(4) 501-10 (2006)). ATR translocation can also be activated by mechanical stress in the nucleus as measured by EM and immunofluorescence (Kumar et al., *Cell*, 158, 633-46 (2014)). MNNG increases downstream ATM activity in cell lines and can cause cell cycle arrest (Stojic et al., *DNA Repair*, 3(8-9):1091-101 (2004)). Disruption of MMR pathway in cell lines with MMR gene pathogenic variants results in a resistance to MNNG-induced cell death (Branch et al., *Nature*, 362:652-4, (1993)). Mismatch-inducing agents have been a useful tool to describe the MMR pathway in cell lines and tumors; however, many of these models use homozygous pathogenic variants in model/reporter cell lines, as opposed to heterozygous commonly observed among patients with LS described here.

Panel sequencing and its limitations: Clinical diagnosis of LS prior to tumor discovery has relied on the Amsterdam II criteria followed by panel sequencing of MMR genes. Of those who are considered to be at-risk, only 27% have pathogenic variants, and 20-40% learn about variants of uncertain significance (VUS), making it difficult to classify their risk (Moriera et al., *JAMA*, 308(15) 1555-65 (2012)). The International Society for Gastrointestinal Hereditary Tumors' (InSiGHT) Variant Interpretation Committee (VIC) was set up to classify variants, and has limited number defined as pathogenic or benign. Multipanel gene testing can test beyond MMR repair genes, and those tested for LS had 5.6% pathogenic variants identified in non-LS genes (Yurgulen, *Gastroenterology*, 149(3):604-13 (2015)).

Due to the large segment of patients that could not be diagnosed with LS from gene panel sequencing, a number of additional tests have been recommended. As stated earlier, the revised Bethesda criteria recommends MSI testing, which uses PCR of microsatellites in tumors (Umar et al., *J Natl Cancer Inst.*, 96(4)261-268 (2004); Parsons et al., *Cancer Res.* 55:5548-50, (1995); Lindor et al., *J Clin Oncol.* 20(4):1043-8 (2002)). Additionally, clinics have implemented measurement of absence of hMLH1 and hMSH2 in tumors by immunohistochemistry. These tumor samples are fixed on slides and observed via microscope for absence or presence (Lindor et al., *J Clin Oncol.* 20(4):1043-8 (2002)). Fecal testing, such as multitarget Cologuard, has been approved as a non-invasive replacement of colonoscopies for CRC screening, (Ahlquist et al. *Dig Dis Sci.*, 60:623-633 (2015)), but it is not used to differentiate LS from other CRCs.

In research settings several tests have been developed using cell-free and non-patient cells to reclassify variants in MMR genes. Cell-free in vitro mismatch repair activity (CIMRA) uses MSH2 deficient nuclear extract mixed with variant or WT MMR protein. This cell-free procedure compares variant to WT function via fluorescent labeled mismatch. (Drost et al., *Genet Med.*, 21(7):1486-96 (2019); Drost et al. *Genet Med.*, 847-56 (2020)). Cell line and yeast models have also been used to reclassify human MMR variants. These assay systems rely on introducing plasmids carrying known variants into a yeast or other reporter cell lines (Takahashi et al., *Cancer Res.* 67:4595-04 (2007)). The limitations with these strategies are they do not use patient cells and it takes time to develop variant plasmids and test in cell-based assays that would be impossible to implement in clinical settings. Also, they are not applicable to identifying LS when variants have not been identified in MMR genes.

Functional Variant Analysis (FVAs): Flow-cytometry based functional variant assays were developed to observe the biological effects of heterozygous pathogenic variants in genes that disrupt genetic pathways. FVAs use fluorescently-labeled antibodies/markers and flow cytometry to measure functional protein changes, such as protein-protein interaction, nuclear transport and/or chemical modifications of proteins, such as phosphorylation. FVAs was first used to rapidly screen VUS in MAP3K1 to diagnose 46,XY gonadal dysgenesis and to uncover unknown mechanisms of the pathogenic pathogenic variants observed. B-lymphoblastoid (LCL) cells of patients with 46,XY gonadal dysgenesis were used in FVAs measuring known protein-protein interactions with MAP3K1 (Loke et al. *Clin Genet.*, 81(3): 272-7, (2012)). The first use of FVAs to determine cancer risk was to evaluated whether pathogenic variants in the BRCA1, BRCA2, and other genes in the double stranded break (DSB) repair pathway altered nuclear localization of the BRCA1 and BRCA2 proteins and phosphorylation of p53 in response to DNA damage caused by diepoxybutane (DEB), mitomycin C (MMC) or bleomycin (Bleo) (Loke et al. *Hum Mol Genet.*, 24:3030-7 (2015)) in cultured LCL cells and subsequently in B cells (Syeda et al., *Genet Med.*, 19(9) 1071-7 (2017)). This test is known as Cancer Risk B, or 'CR-B' and is in development for clinical use to diagnose hereditary breast and ovarian cancer (HBOC). Cancer risk in this test is presented as a risk classification score, which combines the individual FVAs, scales the results and has clear cutoffs for pathogenic and benign results. FVAs have not been previously used in detecting deficiencies in MMR pathway and the diagnosis of LS.

SUMMARY OF DISCLOSURE

This disclosure is directed to methods and compositions for diagnosing and/or treating LS and assessing germline risks of cancer based on analysis in cells of proteins in the DNA MMR pathway. Pathogenic variants in genes within this pathway, (for example, MLH1, MSH2, PMS2, MSH6 and others) may cause severe DNA repair defects, resulting in cellular lethal or cancer in the homozygous state. In the heterozygous state, pathogenic variants in these genes cause LS. The methods disclosed herein measure functionality of each molecular phenotype caused by variants in these genes that are indicative of mutational status and, therefore, germline genetic risk. Identification of these mutational effects in the absence of identifiable germline pathogenic variants or in the presence of identifiable variants can be implemented either as an adjunct to DNA sequencing, especially for annotating variants of uncertain significance, or as a standalone method for diagnosis.

The methods disclosed herein are particularly useful in at least two aspects: (i) the present methods provide functional annotation of VUS identified by genetic sequencing; and/or (ii) the present methods permit diagnosis of LS and evaluation of germline risks of cancer not identified by DNA sequencing of MMR genes. Individuals from high-risk LS families comprise about 5-10% of incident cases of colorectal cancer. Among these individuals, germline pathogenic variants in the MMR genes can be detected in 27% of cases. In 20-40% of DNA sequencing tests, VUS are identified. Annotating variants provide difficulties for accurate diagnosis of patients. In 20-40% of cases, a pathogenic or benign variant cannot be found in a known risk gene. In these cases, MSI or MMR protein absence is measured in the tumor to determine germline predisposition. Research methods have been developed to annotate variants, but these largely rely on cell-free models (CIMRA) or use of cells not from patients (yeast or cell lines).

In addition to categorizing variants, these novel methods may also represent an alternative to genomic sequencing and tumor analysis for identifying functionally important genetic variants that may contribute to pathogenicity that is not observed by sequencing. Most sequencing methods are limited in scope and depth with certain genomic regions being difficult to capture, amplify or assemble. These limitations commonly result in finished sequences that comprise less than the whole of the desired region. Thus, important functional variants may be missed. A direct functional test at protein level bypasses this concern, by querying whether a key biological function is being compromised and, thus, might be more sensitive and specific for identifying genetic risks. This type of assay is also more direct than measuring MSI and/or MMR protein absence in tumors, and provides a means of diagnosis before tumor formation. Because these assays use standard reagents (commercial antibodies) and readily available technology (flow cytometry), they lend themselves to ease of adoption in the research and clinical laboratory environments with minimal change of equipment and workflow.

In an aspect, this disclosure provides methods of diagnosing and treating a subject who has or is suspected of having Lynch Syndrome (LS) and/or who has an increased germline risk of developing cancer, the method comprising: (a) treating a population of cells from a sample isolated from the subject with a DNA mismatch-inducing agent; (b) measuring in the population of cells, at least one functional activity of a mismatch repair (MMR) pathway gene; (c) comparing the at least one functional activity measured with a control value obtained from a control population of cells treated with the DNA mismatch-inducing agent; and (d) categorizing the MMR pathway gene as (i) functional, (ii) having loss of function, (iii) having a gain of function or (iv) having a partial-loss of function, based on the comparing step (c), wherein if the MMR pathway gene is categorized as having loss of function then the subject is determined to have an increased risk of having LS and/or an increased risk of developing cancer.

In some embodiments, the DNA mismatch-inducing agent is selected from the group consisting of $S_N1$ DNA alkylators, 8-oxoguanine, 6-thioguanine (6-TG), fluoropyrimidines, cisplatin, radiomimetic agents, radiation, and UV light. In certain embodiments, the $S_N1$ DNA alkylators are selected from the group consisting of N-methyl-N'-nitro-N-nitrosoguanidine (MNNG), N-methyl-N-nitroso-p-toluenesulfonamide (Diazald®), methylnitrosourea (MNU), procarbazine, and temozolomide. In certain embodiments, the fluoropyrimidines are selected from the group consisting of 5-fluorouracil (FU), and 5-fluoro-2'-deoxyuridine (FdU). In certain embodiments, the radiomimetic agents are selected from Diepoxybutane, Mitomycin C, and Bleomycin. In some embodiments, the DNA mismatch-inducing agent is N-methyl-N'-nitro-N-nitrosoguanidine (MNNG), or N-methyl-N-nitroso-p-toluenesulfonamide, or both N-methyl-N'-nitro-N-nitrosoguanidine and N-methyl-N-nitroso-p-toluenesulfonamide.

In some embodiments, the at least one functional activity of a MMR pathway gene is: (a) the subcellular localization of the protein expressed by the MMR pathway gene, (b) a post-translational modification of the protein expressed by the MMR pathway gene, or (c) both the subcellular localization and the post-translational modification of the protein expressed by the MMR pathway gene.

In some embodiments, the at least one functional activity of a MMR pathway gene is selected from the group consisting of MLH1 nuclear localization, MSH2 nuclear localization, BARD1 nuclear localization, PMS2 nuclear localization, BRCA2 nuclear localization, p53 phosphorylation, ATM phosphorylation, and ATR phosphorylation.

In some embodiments, an antibody or binding fragment thereof is used for measuring the at least one functional activity of a MMR pathway gene.

In some embodiments, measuring the at least one functional activity comprises a flow cytometry assay.

In some embodiments, the control comprises a value corresponding to the at least one functional activity measured from the control population of cells, or one or more subcellular components, having a known benign FVA result or a known pathogenic FVA result.

In some embodiments, the known pathogenic FVA result is measured from the control population of cells, or one or more subcellular components, having a variant gene associated with a defective MMR pathway.

In some embodiments, the known benign FVA result is measured from the control population of cells, or one or more subcellular components, having a variant gene associated with a normal functioning MMR pathway.

In some embodiments, the at least one control value is established at an earlier time.

In some embodiments, the increased risk of having LS and/or the increased risk of developing cancer in the subject is provided by a risk score.

In some embodiments, the method further comprises assessing efficacy of a treatment of Lynch syndrome.

In some embodiments, the method further comprises assessing likelihood of primary and secondary cancers in subjects with LS.

In some embodiments, the method further comprises utilizing optical properties of cells to determine changes in size and complexity in diagnosis of LS.

In another aspect, this disclosure provides methods for screening a sample for functionality of at least one gene in the mismatch repair (MMR) pathway, the method comprising: (a) treating a population of cells from the sample with a DNA mismatch-inducing agent; (b) measuring in the population of cells at least one functional activity of a mismatch repair (MMR) pathway gene; (c) comparing the at least one functional activity measured with a control value obtained from a control population of cells treated with the DNA mismatch-inducing agent; and having a wild type DNA MMR pathway; and (d) categorizing the MMR pathway gene as (i) functional, (ii) having loss of function, (iii) having a gain of function or (iv) having a partial-loss of function, based on the comparing step (c).

In some embodiments, the population of cells from the sample comprises an introduced genetic variant or an expression plasmid.

In some embodiments, the DNA mismatch-inducing agent is selected from the group consisting of SN1 DNA alkylators, 8-oxoguanine, 6-thioguanine (6-TG), fluoropyrimidines, cisplatin, radiomimetic agents, radiation, and UV light. In certain embodiments, the SN1 DNA alkylators are selected from the group consisting of N-methyl-N'-nitro-N-nitrosoguanidine (MNNG), N-methyl-N-nitroso-p-toluenesulfonamide (Diazald®), methylnitrosourea (MNU), procarbazine, and temozolomide. In certain embodiments, the fluoropyrimidines are selected from the group consisting of 5-fluorouracil (FU), and 5-fluoro-2'-deoxyuridine (FdU). In certain embodiments, the radiomimetic agents are selected from Diepoxybutane, Mitomycin C, and Bleomycin. In certain embodiments, the DNA mismatch-inducing agent is N-methyl-N'-nitro-N-nitrosoguanidine (MNNG), or N-methyl-N-nitroso-p-toluenesulfonamide, or both N-methyl-N'-nitro-N-nitrosoguanidine and N-methyl-N-nitroso-p-toluenesulfonamide.

In some embodiments, the at least one functional activity of a MMR pathway gene is: (a) the subcellular localization of the protein expressed by the MMR pathway gene, (b) a post-translational modification of the protein expressed by the MMR pathway gene, or (c) both the subcellular localization and the post-translational modification of the protein expressed by the MMR pathway gene.

In some embodiments, the at least one functional activity of a MMR pathway gene is selected from the group consisting of MLH1 nuclear localization, MSH2 nuclear localization, BARD1 nuclear localization, PMS2 nuclear localization, BRCA2 nuclear localization, p53 phosphorylation, ATM phosphorylation, and ATR phosphorylation.

In yet another aspect, this disclosure provides kits for screening a sample for functionality of at least one gene in the mismatch repair (MMR) pathway, wherein the kit comprises: (a) one or more antibodies for detecting at least one of MLH1, MSH2, PMS2, ATM, Phospho-ATM, ATR, Phospho-ATR, BRCA2, P53, Phospho-P53, BARD1, or Ribosomal s6; (b) a universal FVA buffer; and (c) control cell samples.

In some embodiments, the kit further comprises one or more of: DAPI, a nuclear enrichment buffer, a red blood cell (RBC) lysis buffer, a DNA mismatch-inducing agent, paraformaldehyde, and/or methanol.

BRIEF DESCRIPTION OF DRAWINGS

FIG. 2A) Dose response and survival counts using trypan blue shows significant toxicity >50 µM MNNG in LCL cells from Group 3 (n=3). FIG. 2B) Utilizing the risk classification score which combines results from MLH1, MSH2 and ATR FVAs, 50-25 µM showed the most significant difference between Group 1 and Group 3 (n=6). FIG. 2C) Comparing MNNG (50 µm) to alkylating agent Diazald (25 µm), shows very similar risk classification scores ($r^2$=0.98) when using the same LCLs (n=6).

FIG. 4A) PMS2 and MLH1 FVA assays measuring nuclear localization showed correlated results as measured by $r^2$>0.8 (n=40). FIG. 4B) BARD1 and MSH2 FVA assays measuring nuclear localization showed correlated results as measured by $r^2$>0.8 (n=40). FIG. 4C) When comparing only Group 1 LCLs with pathogenic variants, there is correlation between ATM phosphorylation and MSH2 nuclear localization FVA assays ($r^2$>0.8; n=20)

(FIG. 5A) MLH1 FVA assay, (FIG. 5B) MSH2 FVA assay, (FIG. 5C) ATR FVA assay and (FIG. 5D) RCS.

(FIG. 6A) Scatter plot of the individual gene that had the VUS or they had more than one VUS across multiple genes. (FIG. 6B) Scatter plot of protein absence as measured by IHC. (FIG. 6C) Scatter plot of methylation of MLH1 promoter site. Pairwise comparison (Kruskal-Wallis) was done on groups with n>3 and p values are indicated.

(FIG. 7A) Scatter plot comparing MSI-H individuals to those in Group 1 and (FIG. 7B) MSI-H individuals to Group 3. P-values indicate significant differences between the two groups. MSI-H overlaps with Group 1 (78% of samples are high risk), although means are significantly different and a minority is at population risk.

(FIG. 8A) over antibody concentration. (FIG. 8B) Cell concentration and (FIG. 8C) Days after staining. Overall, assays are reproducible if: (FIG. 8A) >0.5 ug of antibody is used, (FIG. 8B) >10,000 cells/100 ul is used and (FIG. 8C) up to 3 days after staining.

(FIG. 12A) MLH1, (FIG. 12B) MSH2, and (FIG. 12C) ATR FVAs of cells with edits in MLH1; (FIG. 12D) MLH1, (FIG. 12E) MSH2, and (FIG. 12F) ATR FVAs of cells with edits in MSH2; (FIG. 12G) RCS of transfected cells with edits in MLH1, (FIG. 12H) RCS of transfected cells with edits in MSH2. Rescue is shown to be significant by pairwise comparison (p<0.05).

(FIG. 13A) MLH1 FVA, (FIG. 13B) MSH2 FVA, (FIG. 13C) ATR FVA, and (FIG. 13D) risk classification score (RCS).

DETAILED DESCRIPTION

Figure 1:
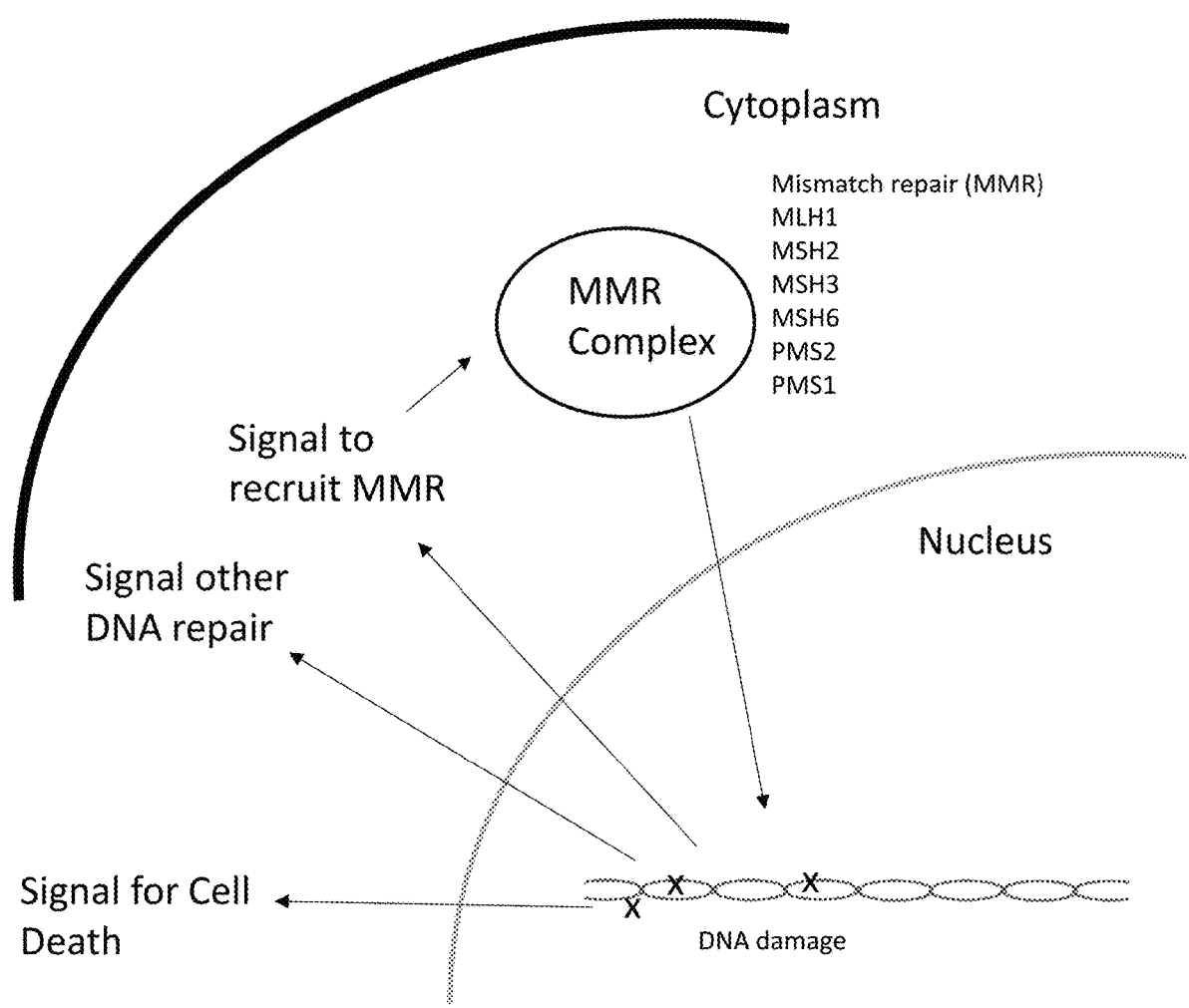
FIG. 1 shows MMR repair pathway initiation. Following mismatches in the DNA, MMR proteins MSH2, MSH6, MLH1 and PMS2 form heterodimers, MutSα (containing MSH2 and MSH6) and MutLβ (containing MLH1 and PMS2), and are transported into the nucleus to the site of mismatch repair. These complexes recruit repair proteins to initiate repair by homologous recombination. They also phosphorylate ATM and ATR which signal to either recruit more MMR proteins or activate P53 for cell death. Mismatches can lead to double stranded breaks which will recruit other DNA repair proteins.

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

Unless otherwise required by context, singular terms shall include pluralities and plural terms shall include the singular. For example, the singular forms "a," "an," and "the" include plural referents unless the context clearly dictates otherwise.

It is noted that terms like "preferably," "commonly," and "typically" are not utilized herein to limit the scope of the claimed subject matter or to imply that certain features are critical, essential, or even important to the structure or function of the claimed subject matter. Rather, these terms are merely intended to highlight alternative or additional features that can or cannot be utilized in a particular embodiment of the present disclosure.

The terms "comprises" and variations thereof do not have a limiting meaning where these terms appear in the description and claims.

The term "substantially" is utilized herein to represent the inherent degree of uncertainty that can be attributed to any quantitative comparison, value, measurement, or other representation.

The term "substantially" is also utilized herein to represent the degree by which a quantitative representation can vary from a stated reference without resulting in a change in the basic function of the subject matter at issue.

As used herein, the term "about" is used to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Ranges and amounts can be expressed as "about" a particular value or range. About can also include the exact amount. Typically, the term "about" includes an amount that would be expected to be within experimental error. The term "about" includes values that are within 10% less to 10% greater of the value provided. For example, "about 10" can include 9, 10, or 11.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure. As utilized in accordance with the present disclosure, unless otherwise indicated, all technical and scientific terms shall be understood to have the same meaning as commonly understood by one of ordinary skill in the art.

These methods disclosed herein for assessing germline risk of LS are based on flow-cytometry based functional variant assays (FVAs) in a cell sample.

In one aspect, this disclosure provides, methods of diagnosing and treating a subject who has or is suspected of having Lynch Syndrome (LS) and/or who has an increased germline risk of developing cancer, the method comprising: (a) treating a population of cells from a sample isolated from the subject with a DNA mismatch-inducing agent; (b) measuring in the population of cells at least one functional activity of an MMR pathway gene; (c) comparing the at least one functional activity measured with a control value obtained from a control population of cells treated with the DNA mismatch-inducing agent; and (d) categorizing the MMR pathway gene as (i) functional, (ii) having loss of function, (iii) having a gain of function or (iv) having a partial-loss of function, based on the comparing step (c), wherein if the MMR pathway gene is categorized as having loss of function then the subject is determined to have an increased risk of having LS and/or an increased risk of developing cancer. Individuals with defects in MMR pathway documented in ClinVar at the NCBI web site of the National Institutes of Health are known to have LS.

Lynch syndrome (LS) is the most common form of hereditary colon cancer, and as used herein can also refer to a disease or disorder resulting from a germline mismatch repair deficiency. Cancers of the stomach, ovaries, endometrium, small intestine, liver, gallbladder ducts, upper urinary tract, brain, skin, and prostate can also occur in LS. Muir-Torre syndrome (MTS) is a form of Lynch syndrome caused by pathogenic variants in the MLH1 gene or the MSH2 gene and is characterized by sebaceous skin tumors in association with internal cancers (e.g. the gastrointestinal tract and/or the genitourinary tract). Predisposition to LS is caused by autosomal dominant heterozygous germline pathogenic variants in mutL homologue 1 (MLH1), mutS homologue 2 (MSH2), mutS homologue 6 (MSH6), or postmeiotic segregation increased 2 (PMS2), or Epithelial Cell Adhesion Molecule (EPCAM).

In some embodiments, the cell sample is isolated from a subject. In certain embodiments, the subject is a human suspected as having LS or who has LS. In certain embodiments, the subject is a human suspected of developing LS. In some embodiments, the subject is a human suspected as having an increased germline risk of developing cancer or who has an increased germline risk of developing cancer. In certain embodiments, the cancer can be colon cancer, stomach cancer, ovarian cancer, endometrial cancer, cancer of small intestine, liver cancer, cancer of gallbladder ducts, upper urinary tract cancer, brain cancer, skin cancer, and/or prostate cancer. In some embodiments, the cell sample comprises any cell type, or one or more subcellular components thereof. In some embodiments, the cell sample comprises non-adherent cells isolated from the subject. In certain embodiments, the cell sample comprises peripheral blood mononuclear cells (PBMC) isolated from whole blood from the subject.

The term "non-adherent cells", as used herein, refers to cells that are free floating in media and not adherent. In some embodiments, non-adherent cells do not adhere to a plate typically used for tissue culture and/or cell expansion. Cells adherent to a plate can become "non-adherent" if loosened off the plate (i.e.: using trypsin to dislodge cells from plate).

The phrase "peripheral blood mononuclear cells" or "PBMCs", as used herein, refer to any peripheral blood cell having a round nucleus, and includes, but is not limited to, lymphocytes (i.e., T cells and B cells), monocytes, neutrophils, eosinophils, and basophils. In specific embodiments, B cells are used in the analysis.

The term "functional variant analysis", "functional assay", "flow variant activity" or "FVA", as used herein, refers to analysis designed to determine the functional phenotype of variants in a gene of interest, i.e., whether a variant in a gene of interest encodes a protein that is (i) functional, (ii) having loss of function, (iii) having a gain of function or (iv) having a partial-loss of function (wherein "functional" refers to changes in protein levels, location, structure, variants or post-translational modifications), or cellular properties that are observably changed due to induction of the MMR pathway (i.e., changes in size of cell, size of nucleus or both; complexity or nuclear organization of the whole cell, or a subcellular component). A variant in a gene leads to a functional change if there is a one standard deviation or greater difference in one or more MMR FVA assay when compared to the functionality from a population of samples with a wild-type or benign variant (FIG. 3). For example, a loss of function occurs when the three or more MMR FVA assays have a greater than one standard deviation loss of function compared to a population with wild-type variant. An example of gain of function is when a pathogenic variant increases in function by greater than one standard deviation (FIG. 12). An example of partial-loss of function occurs when two or less MMR FVA assays have a greater than one standard deviation loss of function compared to a population with wild-type variant and at least one MMR FVA has less than one standard deviation difference compared to the wild-type variant population. In some embodiments, the FVA is designed to evaluate the functionality of variants of genes in the MMR pathway. In some embodiments, the FVA is designed to identify pathogenic variants of genes in the MMR pathway. Such genes can include, but are not limited to, MLH1, MSH2, PMS2, ATM, ATR, BRCA2, P53 and BARD1.

The functionality of the protein expressed from a MMR pathway gene can be evaluated in various assays (after a population of cells is treated with a DNA mismatch-inducing agent) depending on the biological functions of the protein, and can in many instances be correlated with pathogenicity of a disease (e.g., LS). In some embodiments, flow cytometry is used to measure the at least one functional activity of a MMR pathway gene, and/or functional protein changes, such as protein-protein interaction, nuclear transport and/or chemical modifications of proteins, such as phosphorylation.

In some embodiments, functionality of variants of genes in the MMR pathway can be measured as increased translocation of the expressed proteins to the nucleus as measured by a ratio of the protein in isolated nuclei to that of whole cell (as observed in the case of FVAs of MLH1, MSH2, PMS2, BRCA2, and BARD1). In certain embodiments, the at least one functional activity of a MMR pathway gene is: (a) the subcellular localization of the protein expressed by the MMR pathway gene, (b) a post-translational modification of the protein expressed by the MMR pathway gene, or (c) both the subcellular localization and the post-translational modification of the protein expressed by the MMR pathway gene. In certain embodiments, functionality of variants of genes in the MMR pathway are measured after a population of cells is treated with a DNA mismatch-inducing agent.

In certain embodiments, the at least one functional activity of a MMR pathway gene is selected from MLH1 nuclear localization, MSH2 nuclear localization, BARD1 nuclear localization, PMS2 nuclear localization, BRCA2 nuclear localization, p53 phosphorylation, ATM phosphorylation, and ATR phosphorylation. In some embodiments, functionality of variants of genes in the MMR pathway can be measured as an increase in phosphorylation of the expressed protein in the whole cell as measured by a ratio of phosphorylated to total protein (for example, as in the case of p53) and/or increased phosphorylation in a subcellular component as measured by the ratio of phosphorylated to total protein (for example, as in the case of ATM and ATR phosphorylation in the nuclei).

These proteins and post-translational modifications can be detected, for example, by an antibody, antigen-binding fragment thereof, or direct binding of a detectable marker (e.g., fluorescent marker). In some embodiments, an antibody used herein can target native and/or post-translational modifications of a protein in order to determine changes in signaling. In certain embodiments, an antibody used herein can be combined with one or more markers of subcellular components, which are then combined to determine subcellular translocation of proteins.

As disclosed herein, "antibody" refers to immunoglobulin molecules and immunologically active portions of immunoglobulin molecules, i.e., molecules that contain an antigen binding site that immunospecifically binds an epitope of an expressed protein of an MMR gene. Antibody encompasses not only whole antibody molecules, but also antibody fragments, as well as variants (including derivatives) of antibodies and antibody fragments. Such antibody or antibody fragments thereof may include, but are not limited to monoclonal antibodies, polyclonal antibodies, humanized antibodies, chimeric antibodies, Fab', F(ab')2, Fab, Fv, rIgG, recombinant single chain Fv fragments (scFv), bivalent or bispecific molecules, diabodies, triabodies, and tetrabodies. In certain embodiments, the antibodies comprise monoclonal antibodies, or fragments thereof. In certain embodiments, the antibodies comprise polyclonal antibodies, or fragments thereof. In some embodiments, the antibodies comprise humanized antibodies, or fragments thereof. In some embodiments, the antibody can comprise a detectable marker. For example, a detectable marker can be a fluorescent marker (e.g., fluorescein isothiocyanate or FITC, rhodamine, or lanthanide phosphors), a chemiluminescent marker, radioisotope, or an enzymatic activity (e.g., horseradish peroxidase, β-galactosidase, luciferase, alkaline phosphatase), that can be detected by optical or colorimetric methods.

In some embodiments, the methods as disclosed herein also consider the use of secondary antibodies, antigen-binding fragments, or other marker that binds to the primary antibody, as an alternative method of detecting proteins or post-translational modifications. For example, a fluorescently-labeled secondary antibody that binds to a primary antibody which binds to a protein of interest can be used in replacement of a fluorescently labeled primary antibody.

In some embodiments, the subcellular localization of an expressed protein of an MMR pathway gene can be determined by the absence or presence of cytoplasmic and/or nuclear markers. In some embodiments, a whole cell can be identified by having the presence of one or more nuclear markers and one or more cytoplasmic markers. In contrast, nuclear-only is defined as having the presence of a nuclear marker and the absence of a cytoplasmic marker. In some non-limiting embodiments, cytoplasmic markers can include, but are not limited to ribosomal S6, actin, cytokeratin 19, GAPDH, HIF1A, iNOS, vimentin, ribosomal s4, ribosomal s11, LAMP1, HSP90, tubulin, cofilin, cyclophilin B, and Cox4. In certain non-limiting embodiments, nuclear markers can include, but are not limited to DAPI, histones, nuclear resident transcription factors, propidium iodide, Hoechst, TO-PRO®-3, SYTOX® and DEADRed®.

Optical properties of light passing through cells, or subcellular components thereof, can determine size (forward scatter light), and complexity (side scatter) of the cells and/or their subcellular components. These properties are changed by defects in the MMR pathway genes because of aberrant protein function (i.e., increased levels of protein in the nucleus causes size and complexity changes). Changes in functionality can also be demonstrated by using optical properties of light passing through cells. For example, if cells have a pathogenic variant resulting in an increase in the transport of MMR proteins in the nuclei due to a feed-forward response that is unable to repair mismatches, then this increase in protein in the nucleus will lead to an increase in nuclear complexity that will be detected by an increase in side scatter intensity. Furthermore, subcellular markers, such as DNA staining (e.g. by DAPI), can also have changes in fluorescent intensity due to changes in DNA organization and DNA condensation due to defects in the MMR pathway. This property is also taken into account in this method of identifying LS.

Figure 3A:
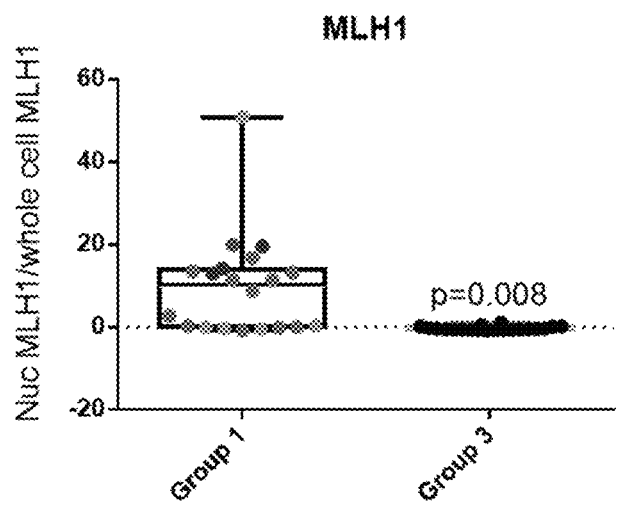
FIG. 3A-3L show FVA assays for MLH1, MSH2, BARD1, PMS2, ATR, ATM, BRCA2 and P53 and combined risk classification score for different groups. The proteins showing significant changes in function between Group 1 (known mutation carriers=positive controls) and Group 3 (family members of mutation carriers without pathogenic variants=negative controls) are displayed above with p values (n=20 per group). MLH1 (FIG. 3A), MSH2 (FIG. 3B), BARD1 (FIG. 3C), and PMS2 (FIG. 3D) staining were compared in nucleus vs whole cell, and ATR (FIG. 3E) and ATM (FIG. 3F) phosphorylation vs total were measured in the nucleus. Additional proteins involved in other DNA repair pathways were tested, for example, BRCA2 staining comparing nucleus vs whole cell (FIG. 3G) and whole cell 9hosphor-P53 vs total P53 (FIG. 3H). Logistic regression of MLH1 (FIG. 3I), MSH2 (FIG. 3J) and ATR (FIG. 3K) resulted in a risk classification score—RCS (FIG. 3L) that was applied to Group 1, Group 2 (individuals without pathogenic variants, but high MSI or missing MMR proteins measured by IHC) and Group 3 (n=60 per group). Dotted line indicates cutoff for MMR deficiencies.
Figure 3B:
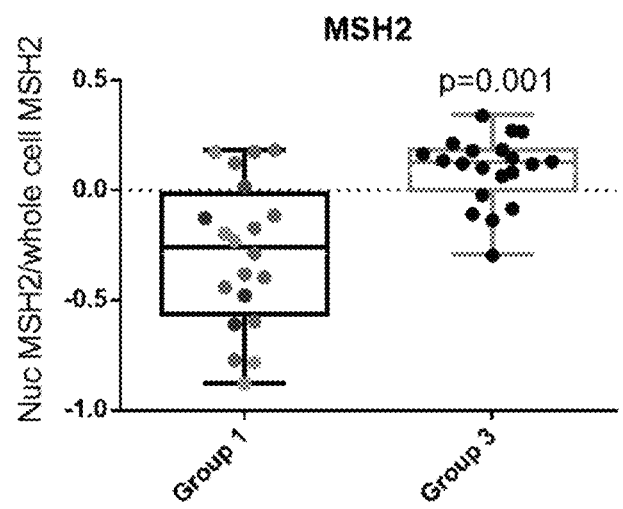
Figure 3C:
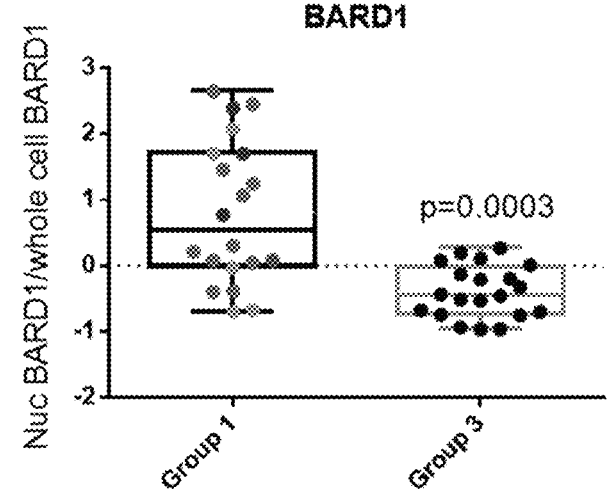
Figure 3D:
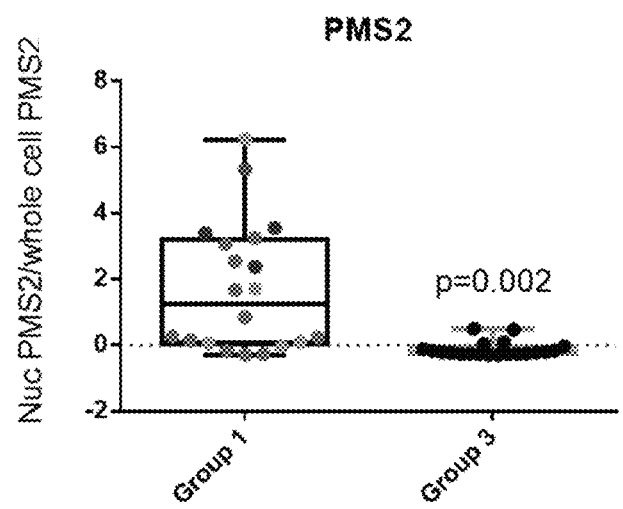
Figure 3E:
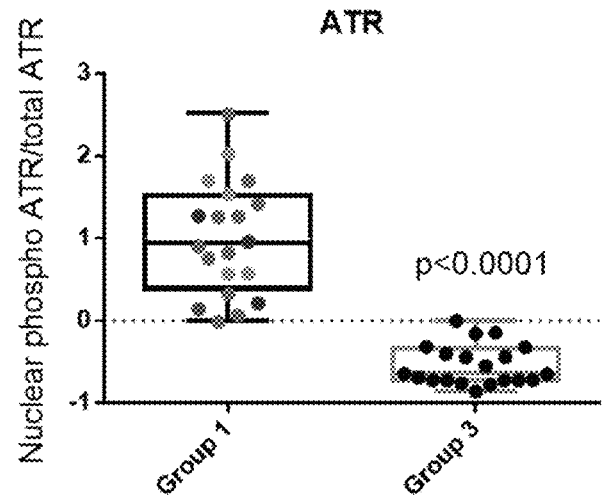
Figure 3F:
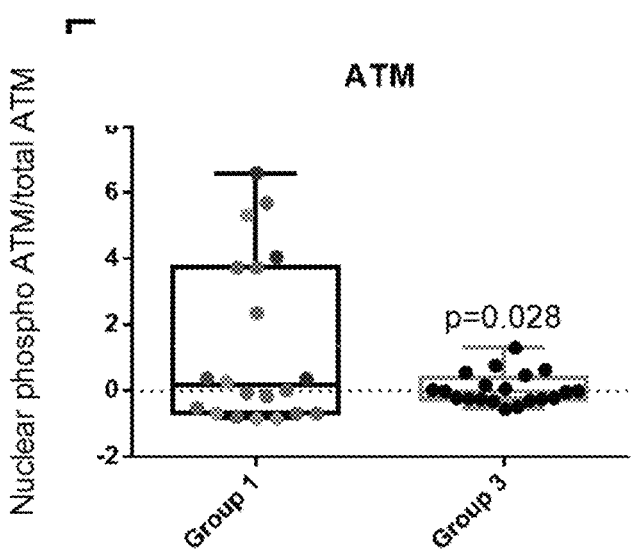
Figure 3G:
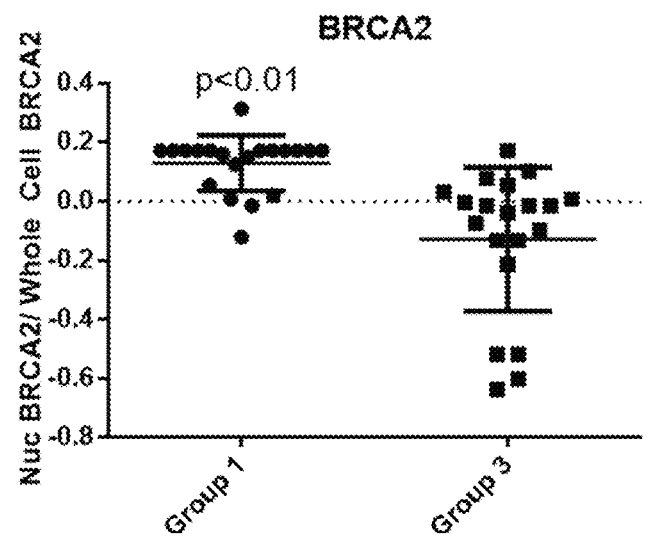
Figure 3H:
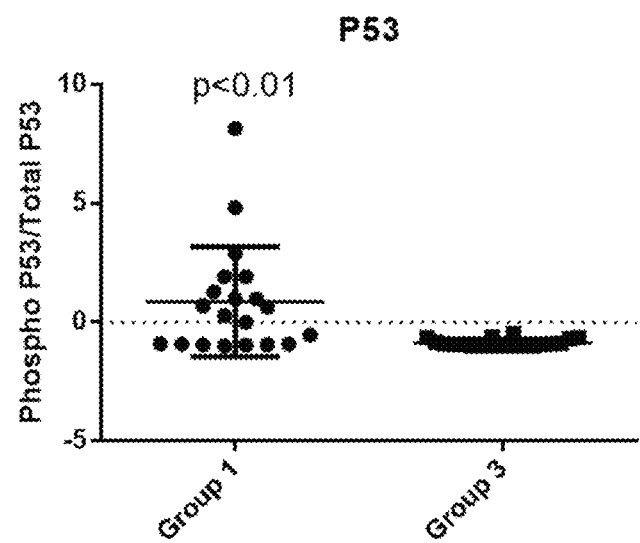
Figure 3I:
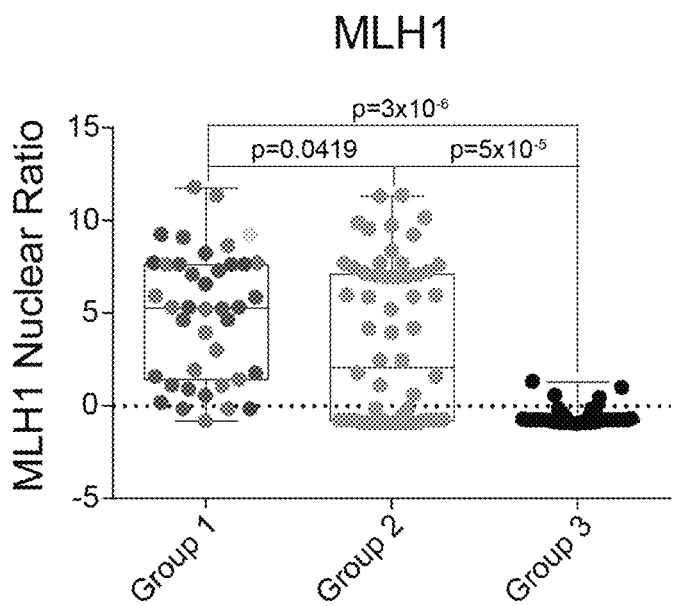
Figure 3J:
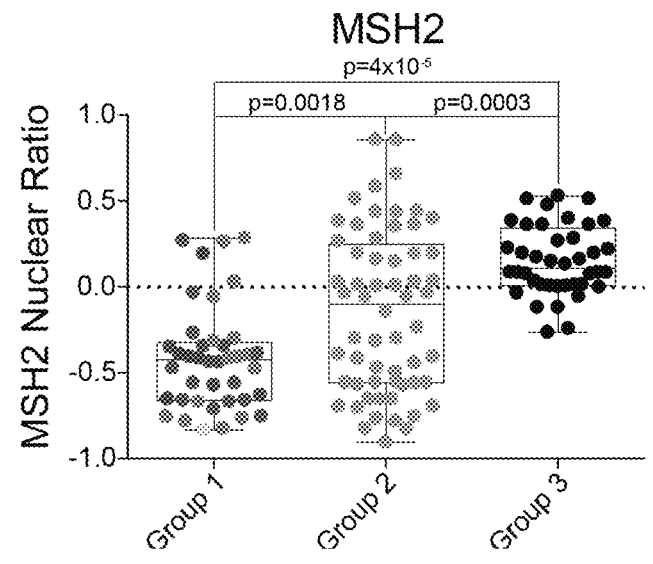
Figure 3K:
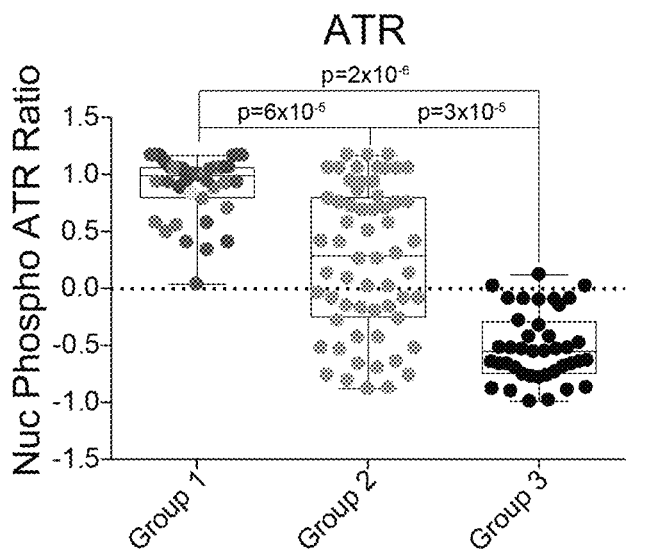
Figure 3L:
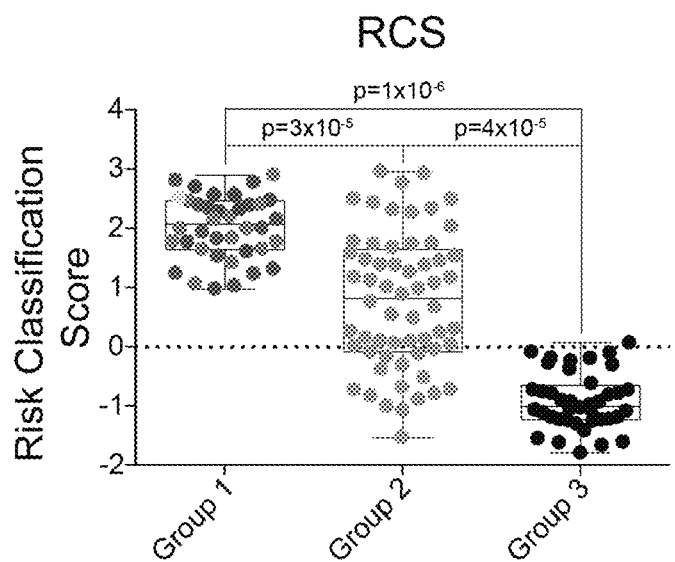

In accordance with this disclosure, a "DNA mismatch-inducing agent" or a "DNA damaging agent" refer to any agent that causes DNA alkylation, DNA adducts, and/or single or oligobase-pair changes. One or more DNA mismatch-inducing agents can be applied to the cells (e.g., PBMCs) to permit manifestation and evaluation of the functionality of variants in MLH1, MSH2, MSH6, PMS2 or other MMR genes, or that have no variant in MMR genes, but have a tumor that is microsatellite instability (MSI)-high. In certain embodiments, the DNA mismatch-inducing agent(s) activate the MMR pathway and redundant repair pathways (double stranded break repair pathway, as shown in FIG. 3G) within the population of cells. In some embodiments, exemplary DNA damaging agents can include agents that cause DNA mismatches, including, but not limited to, radiation, UV light (200-400 nm) and radiation at other frequencies (e.g., X-ray, gamma rays); thermal disruption; chemical compounds such as known mutagens (e.g., N-methyl-N'-nitro-N-nitrosoguanidine (MNNG) and N-methyl-N-nitroso-p-toluenesulfonamide (Diazald®)), and combinations thereof. In some embodiments, a DNA mismatch inducing agent is selected from the group consisting of $S_N1$ DNA alkylators, 8-oxoguanine, 6-thioguanine (6-TG), fluoropyrimidines, cisplatin, radiomimetic agents, radiation, and UV light. In some embodiments, the SN1 DNA alkylators are selected from N-methyl-N'-nitro-N-nitrosoguanidine (MNNG), N-methyl-N-nitroso-p-toluenesulfonamide (Diazald®), methylnitrosourea (MNU), procarbazine, and temozolomide; the fluoropyrimidines are selected from 5-fluorouracil (FU), and 5-fluoro-2'-deoxyuridine (FdU); and the radiomimetic agents are selected from Diepoxybutane, Mitomycin C, and Bleomycin. In certain embodiments, the DNA damage produced in this assay is the formation of O4-methylguanine DNA adduct. When these adducts are formed it leads to a G:C to A:T formation, and this signals MMR proteins. Thus, in some embodiments, the DNA mismatch-inducing agent activates the MMR pathway. In certain embodiments, the DNA damaging agent is MNNG and/or Diazald®. MNNG and/or Diazald® are known to produce the O4-methylguanine adduct form of DNA damage.

In some embodiments, the cells treated with a DNA mismatch-inducing agent are then analyzed in one or more FVA assays. The results are then compared to control values produced from controls samples run concurrently in the same run, or in a previous run. In some embodiments, control samples are pre-stablished samples known to: (1) show a pathogenic FVA result (indicating a person with LS) or (2) show a benign FVA result (person without LS or population control). Control samples that have a pathogenic FVA are validated to also have a pathogenic mutation and samples used for benign FVA controls have a benign variant or population variants that result in normal functioning MMR pathway. These control samples allow for calibration and validation that experiment was run accurately. In some embodiments, controls are established prior to testing samples through multiple FVA testing that show consistently either pathogenic or benign results.

In certain embodiments, the methods disclosed herein encompass using FVAs to assay subcellular second messengers within the nucleus, for example ATM and ATR phosphorylation.

The results here demonstrate for the first time use of MNNG in combination with flow cytometry. As demonstrated herein, FVA assays are faster, high-throughput, and more sensitive than conventional assays.

MSI and immunohistochemistry (IHC) testing of tumors require a tumor that is already formed and samples taken from the tumor before LS is determined. In contrast, FVAs are direct and can detect germline pathogenic variants before tumor formation. Cell-free and cell line assays are slower than FVAs, do not always consider VUS nor defects in the MMR pathway that are not detectable by DNA sequencing, and do not use original patient cells.

Based on the results of the FVA analysis, it can be determined whether the variants in the MMR genes are causal for LS-associated cancers. The effects of such variants can be determined even when they cannot be identified by contemporary DNA sequencing methods. It should be noted that the present methods quantify the likelihood or risk of developing colorectal cancer, endometrial cancer, and other cancers, for example, stomach cancer, ovarian cancer, cancer of small intestine, liver cancer, cancer of gallbladder ducts, upper urinary tract cancer, brain cancer, skin cancer, and/or prostate cancer. For example, when the FVA assay is a MLH1 nuclear localization assay, a substantial increase of MLH1 nuclear localization in cells being tested as compared to normal cells indicates that the MMR variant in the subject is associated with increased likelihood or risk of cancer.

In certain embodiments, diagnosis and/or treatment of LS by FVA comprises determining a risk score. A risk score can be derived from one or more functional assays that is normalized to controls and compared to a cut off(s) to determine if an individual has LS and/or is at increased risk for LS-related cancers, and/or an increased germline risk of developing cancer. As defined herein, "risk score" refers to changes in the at least one functional activity measured that predict risk for developing LS-related cancer and/or an increased germline risk of developing cancer. In some embodiments, risk assessment can be measured as: weighted measure of three FVA assays on MMR proteins that are combined using logistical regression and zero centered/cut-off so that pathogenic risk score is a positive number and benign risk score is a negative number.

In the case of determining LS this score has a binary outcome, where, for example, if a patient has a positive score then they are diagnosed with LS, while if a patient has a negative risk score, they do not have LS. For risk of developing cancer, for example, the risk score of less than 1 standard deviation from a population with benign or wild-type variant is considered low risk. An example of high risk is when there is a greater than 2 standard deviation change from the population with wild-type/benign variant.

In certain embodiments, diagnosis and/or treatment of LS by FVA can be done as either stand alone or as a companion to genetic testing. When used as a companion to genetic testing, FVA analysis can validate pathogenic or benign variants, determine if polygenic or other factors (e.g., epi-genetic and/or environment) can affect LS diagnosis, and annotate VUS as pathogenic or benign.

In some embodiments, the method further comprises assessing efficacy of a treatment of Lynch syndrome. This test would be administered prior to administering a surgery/drug to treat cancer resulting from LS, a drug to reduce risk of developing cancer due to LS or immunotherapy for treatment of cancer. For example, patients with LS and cancer are sensitive to checkpoint inhibitors such as PDL-1 inhibitor Pembrolizumab, then this FVA LS method can be used to screen patients with colon cancer for LS to determine whether they will be responsive to pembrolizumab.

Figure 14:
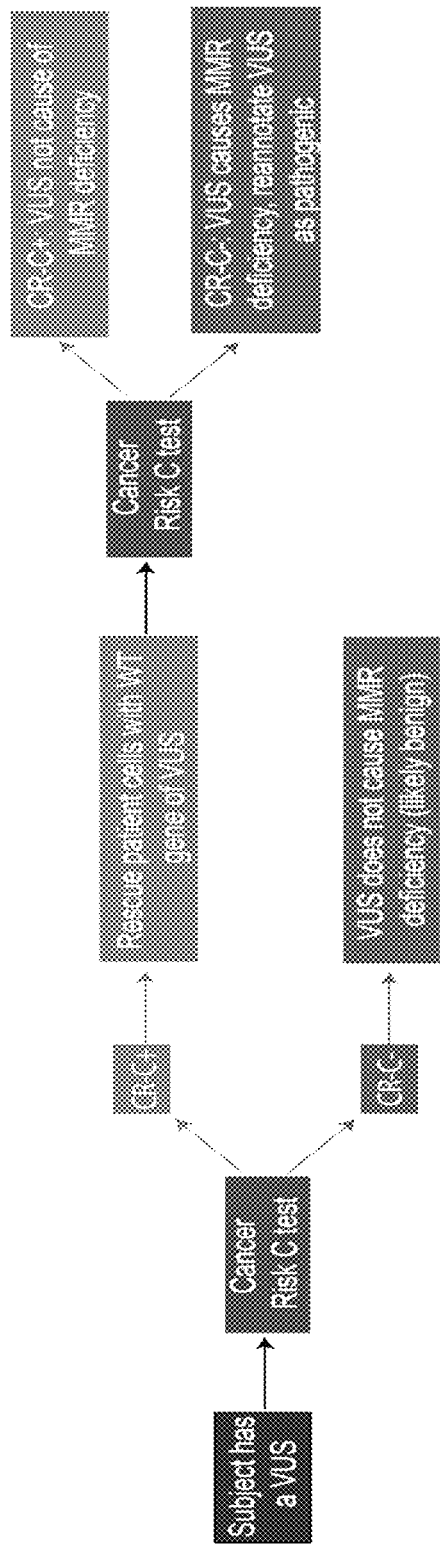
FIG. 14 shows how to use Cancer Risk C to annotate VUS. Potential workflow for integration of CR-C on clinical practice.

In certain embodiments, FVA diagnosis of LS can be used to determine preventative, early intervention or late-stage therapy (e.g. chemotherapy, immunotherapy, radiation, and surgery). The current approach for diagnosis and treatment of LS by NCCN guidelines first looks at family history of genetic testing for LS, if a pathogenic variant is known in the family, the individual is tested for the presence of this variant. If the individual has that variant, then the individual undergoes preventative or early intervention. If a familial pathogenic variant is not present, then the individual undergoes colonoscopy and other cancer screenings at regular prescribed intervals. Individuals who have family history of LS and no known pathogenic variant undergo genetic testing. Those with a pathogenic variant are also considered to have Lynch syndrome and to be at high risk for LS-related tumors. Those not tested, with VUS or no detectable pathogenic variant are unable to be categorized as having LS nor at high-risk for LS-related cancers and undergo tailored surveillance. This group is of indeterminate state for diagnosis of LS and the test described here can diagnose these individuals as having LS and at being at increased risk for cancer (FIG. 14).

As used herein, the term "aggressive cancer treatment" refers to a treatment regimen that is determined by a medical professional or team of medical professionals and can be specific to each subject. In certain embodiments, a subject predicted to have LS or be at increased risk for developing a secondary cancer, using the methods and kits disclosed herein, would be treated using an aggressive cancer treatment. Whether a treatment is considered to be aggressive will generally depend on the cancer-type, the age of the patient, and other factors known to those of skill in the art. An aggressive cancer treatment and/or surveillance strategy is defined by the National Comprehensive Cancer Network (NCCN), and has been defined in the NCCN Guidelines® as including one or more of: increased surveillance such as colonoscopy every 1-5 years, chemoprevention, such as 600 mg of aspirin daily, increased surveillance and testing for other cancer types (for example, endometrial, ovarian, urothelial, gastric and small bowel, pancreatic, prostate, breast, and/or brain) and/or prophylactic surgery, such as bilateral salpingo-oophorectomy (BSO). Patients of reproductive age are advised to have prenatal diagnosis. Guidelines for clinical practice are published in the National Comprehensive Cancer Network (NCCN Guidelines® Colorectal Version 1e.2020, updated Jul. 21, 2020, available at NCCN.org).

Additional therapeutic options may include, but are not limited to: chemotherapy, radiotherapy, surgery and targeted therapy such as immunotherapy. Chemotherapy refers to chemical agents that can be used to prevent, slow and kill cancer cells and tumors as a result of LS. Chemotherapy can include, but is not limited to treatment with oxaliplatin, 5-FU, irinotecan and aspirin (as a prophylaxis). Radiotherapy refers to using irradiated wavelength or particles to prevent, slow and kill cancer cells and tumors as a result of LS. Radiotherapy typically includes external beam radiation therapy (EBRT) at 2-3 grays dose per fraction. Immunotherapy refers to the use of antibodies to target specific proteins in the checkpoint pathway to prevent, slow and kill cancer cells and tumors as a result of LS. Immunotherapy can include, but is not limited to treatment with pembrolizumab.

In certain embodiments, if the FVAs provide pathogenic results for patients with primary cancers, then results can be used to determine likelihood of developing additional primary cancers based on the level of deficiency in the MMR pathway. For example, the risk classification score provides a measure for which one can determine likelihood of developing primary and secondary cancers, particularly if they are in the high-risk range (risk score of 2 or greater standard deviations from mean of population with wild-type variant). If a patient has a primary cancer and falls into this range, then they have a higher likelihood of developing a secondary cancer compared to those who have a risk score of less than two standard deviations from wild-type population.

In certain embodiments, if the FVAs demonstrate MMR deficiencies, then the methods disclosed here can assess efficacy of a treatment of LS, such as immunotherapy. If cancer in LS patients is more sensitive to PDL-1 inhibitors (pembrolizumab), then this method can be used to screen those with cancer who also have LS.

In another aspect, this disclosure provides methods for screening a sample for functionality of at least one gene in the MMR pathway, the method comprising: (a) treating a population of cells from the sample with a DNA mismatch inducing agent; (b) measuring in the population of cells at least one functional activity of a MMR pathway gene; (c) comparing the at least one functional activity measured with a control value obtained from a control population of cells treated with the DNA mismatch-inducing agent; and having a wild type DNA MMR pathway; and (d) categorizing the MMR pathway gene as (i) functional, (ii) having loss of function, (iii) having a gain of function or (iv) having a partial-loss of function, based on the comparing step (c).

In certain embodiments, the population of cells being screened comprises a genetic variant introduced by gene editing (FIG. 12-13). Annotating variants as pathogenic traditionally require genetic sequencing information and a decision from an expert panel who have observed that variant to lead to MMR-deficiency. This method is able to ID new pathogenic variants, as well as validate or re-annotate pathogenic, benign or variants of uncertain significance (VUS) without traditional sequencing and a panel of experts (FIG. 14). Majority of variants are categorized as variants of uncertain significance (VUS). Sequencing results of a VUS in mismatch repair genes does not diagnose LS, even though they may have LS (as observed by the Bethesda criteria). The methods disclosed herein can re-annotate VUS to benign or pathogenic. Utilizing these methods on edited cells, tissue with prior genetic testing (pathogenic, uncertain or benign) or tissue without prior genetic testing can be used to understand the mechanisms of MMR pathway, and annotate variants for future diagnosis. For example, group 2 data (FIG. 3I-L) have no pathogenic variants according to sequencing, yet can be re-annotated using the methods disclosed herein (FIG. 14).

In yet another aspect, the disclosure provides kits for screening a sample for functionality of at least one gene in the MMR pathway, wherein the kit comprises: (a) one or more antibodies for detecting at least one of MLH1, MSH2, PMS2, ATM, Phospho-ATM, ATR, Phospho-ATR, BRCA2, P53, Phospho-P53, BARD1, or Ribosomal s6; (b) a universal FVA buffer; and (c) control cell samples. In some embodiments, a universal FVA buffer comprises a balanced buffer with antibodies or serum as a blocking agent and is given at concentrations of 100 μl per 100,000 cells.

In some embodiments, the control cell samples (pathogenic and benign) have either known variants for pathogenic control cells (for example: MLH1 c.1852_1854delAAG, MSH2 c.2236_2237insA, PMS2 c.400C>T, and MSH6 c.900insG) or have benign or wild-type variants (for example: MSH2 c.287G>A, MSH6 c. 129T>C, and MLH1 c. 2570G>T). Those with pathogenic variants have been described to have LS and be at increased risk for cancers based on results submitted to ClinVar.

In some embodiments, the kit further comprises: DAPI, a nuclear enrichment buffer, an RBC lysis buffer, a DNA mismatch inducing agent (e.g. MNNG), paraformaldehyde (e.g. at about 37%), or methanol (e.g. at about 99%).

In some embodiments, the kit further comprises LS analysis software. This software imports and analyzes raw data from the flow cytometer. This analysis includes, but not limited to, normalizing the data, combining individual assays, calculating a risk classification score (RCS) from more than 1 assay and using the RCS to diagnose LS. For example, a score of a positive number (i.e.: +0.5) can be interpreted as having LS, while a negative score (i.e.:−0.5) does not have LS.

Without limiting the disclosure, a number of embodiments of the disclosure are described below for purpose of illustration.

This disclosure will be further described in the following examples, which do not limit the scope of the claimed subject matter.

EXAMPLES

The examples that follow are illustrative of specific embodiments of the disclosure, and various uses thereof. They are set forth for explanatory purposes only and should not be construed as limiting the scope of the disclosure in any way.

Example 1. Nuclear Localization and Nuclear Second Messenger Assay for MMR Deficiencies This example describes exemplary protocols and reagents for the FVA assays to diagnose LS.

Staining Protocol
1. Use 2-8 ml of freshly drawn blood in an ACD or Na citrate tube (not older than 3 days after collection, ideally within 24 hours), pour into a sterile 50 ml conical tube with 3× volume with red blood cell (RBC) removal buffer (selectively lyses RBC with minimal effect on leukocytes) incubate on a rotator for 5 minutes (no more).
2. Spin at 1080 g for 5 minutes to pellet cells. Gently remove supernatant while maintaining intact pellet. Rinse with 20 ml of 1×PBS and repeat step two more times. Pellet should be a yellowish-white color.
3. Carefully remove supernatant and add 1 ml of pre-warmed culture media (37° C.). Resuspend pellet. Put suspended cells in media into barcoded 2 ml Matrix tubes (screw cap or silicone push caps) and add 50 μM MNNG. Keep lid on tube loose to allow air circulation. Culture cells overnight (24 hours) at 37° C. in a 5% $CO_2$ incubator before FVAs. RMAS is added at 1:1000 (v/v) concentration in media. In the case of suspended LCL cells, add MNNG directly into media and incubate overnight.
4. After 24 hours add 37% paraformaldehyde (4% final concentration) and incubate for 5 minutes. Spin at 1080 g for 5 minutes to pellet cells. Decant supernatant and loosen cells by vortexing mid speed. Fix and resuspend cells in frozen methanol.
5. Count cells and take 100,000 cells. Wash with universal FVA buffer and spin at 1080 g for 5 min. Decant and wash and spin again with universal FVA buffer.
6. Nuclear isolation buffer is added to pellet and resuspended to isolate nuclei. Cells are incubated for 10 minutes at 4° C. on a rocker.
7. Samples are spun at 1080 g for 5 min and nuclear buffer is decanted.
8. Cells are resuspended in universal FVA buffer and blocked for 1 hour.
9. During this time, fluorophore conjugated antibodies against MMR proteins and ribosomal s6 are quenched.
10. Fluorophore conjugated antibodies are added to suspended cells and incubated at 4° C. overnight on a rocker.
11. After incubation cells are washed in universal FVA buffer and spun at 1080 g for 5 min. This is repeated 3 times.
12. Cells are finally resuspended in universal FVA and stained with DAPI. Cells are stored in 4° C. in the dark until use.

Flow Cytometry and Analysis Protocol
1. Gently shake 96-well plate on vortex and load plate on HTS plate loader on BD Canto II.
2. Ensure HTS is securely connected to SIT on flow machine.
3. Ensure all controls and stained samples are in a 96-well U-bottom plate (samples could have been processed in this plate as well).
4. All experiments were standardized with blank unstained methanol treated sample and single-color controls.
5. Stained known positive control (with pathogenic variants) and negative control (with population risk variants) are run with each plate to calibrate FVA.

6. Plates have 3 technical replicates; coefficient of variation is calculated and means are taken for analysis.
7. FlowJo software is used for analysis. Preset gates measuring s6 and DAPI without s6, are used to isolate whole cell and nuclear only signal, respectively.
8. Nuclear translocation analysis: In the example of MLH1, nuclear MLH1 is normalized by taking the number of MLH1 positive nuclei (DAPI without s6) and dividing by total nuclei (DAPI without s6). Whole cell MLH1 is normalized by taking the number of MLH1 positive whole cell (with s6) and dividing by total whole cell (with s6). Then, normalized nuclear MLH1 is divided by normalized whole cell MLH1 to give a ratio of number of cells with nuclear translocation. This is done for MLH1, MSH2, PMS2, and BARD1 FVA assays.
9. Nuclear second messenger analysis. In the example of ATR, only isolated nuclei (DAPI without s6 signal) are considered. Phosphorylated ATR is divided by total ATR to normalize the ATR activity in the nuclei. This is done for ATR and ATM FVA assays.
10. Using the coefficients of each FVA, and the flow results, a risk score was established, categorizing samples as pathogenic or benign.

Light Scatter Measurements
1. In addition to FlowJo analysis, BD Diva software can also export numbers of raw data.
2. Following run, export data in csv format.
3. Each individual well will have gate data, as well as FSC, SSC and Pacific Blue intensity, area and height.
4. Using this data, light scatter measurements from flow cytometer are normalized to cell and/or nuclei counts to determine morphological changes.

Conjugate Fluorophore to Antibody
Use Novus Biologicals Kit: Lightning Link R-Phycoerythrin Conjugation Kit Protocol #703-0010.
1. Add 1 ul of LL-Modifier reagent (10× stock) for each 10 ul of antibody to be labeled (10 ul total). Mix gently.
2. Remove the screw cap from the vial of Lightning-Link-Antibody mix and pipette the mix directly into the lyophilized material in the vial. Resuspend gently by withdrawing and re-dispensing the liquid once or twice using a pipette, incubate overnight at room temperature in drawer (dark).
3. Store at −20° C.

Permeabilizing Agent
100% ice-cold Methanol

Figure 2A:
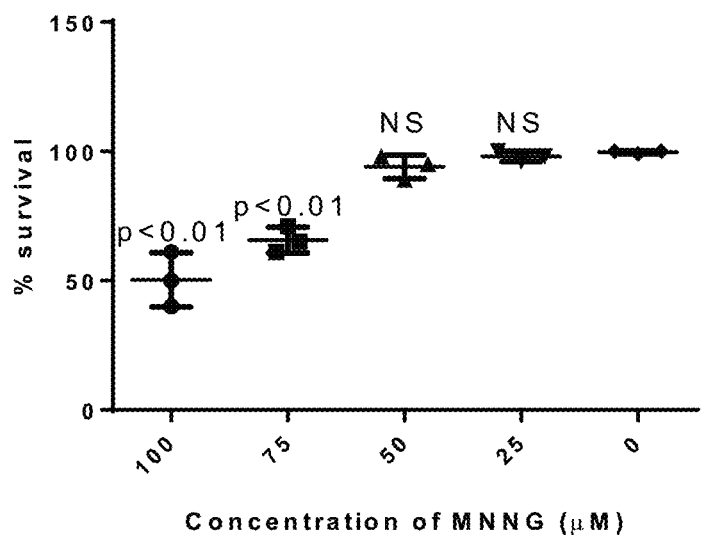
FIG. 2A-2C show optimized MNNG dose response. MNNG is an alkylating agent that can induce mismatches; however, at high concentrations, it is toxic to normal cells.
Figure 2B:
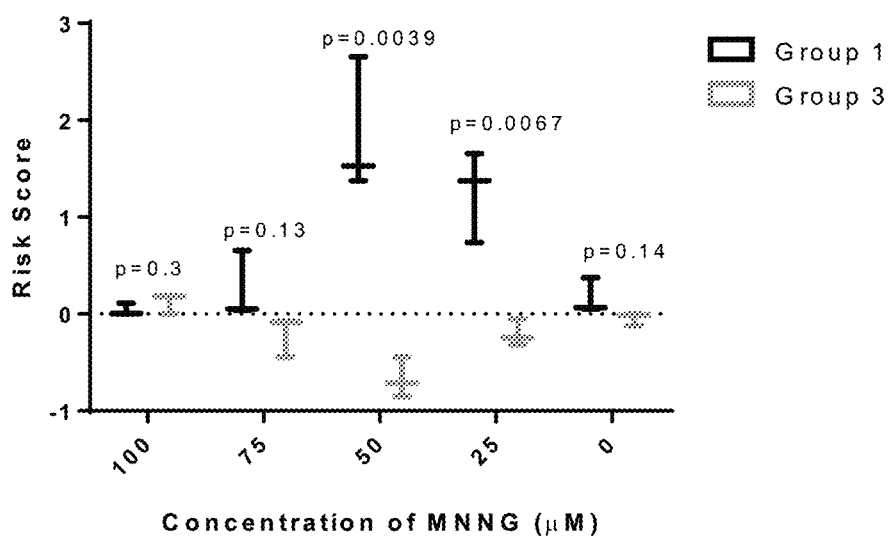
Figure 2C:
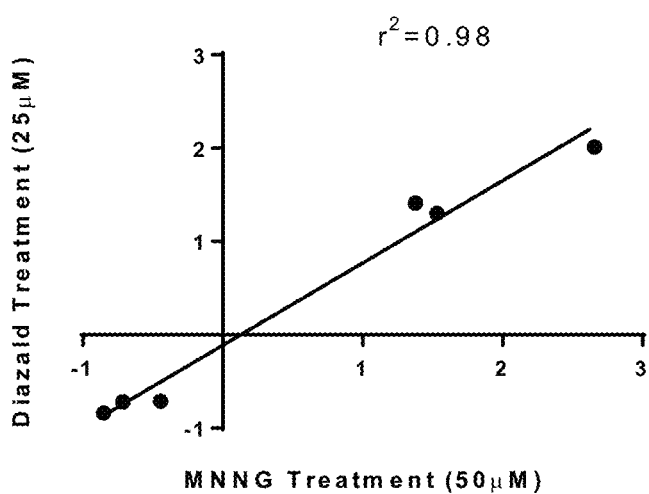

Cytolysis Buffer
10 mM Tris-HCl (pH 7.4)
10 mM NaCl
10 mM MgCl2
2 mM EDTA
10% glycerol
1% NP-40
Complete protease inhibitors—Roche
Universal FVA buffer (Good for 6 months at 4° C.)
50 mM Tris-HCl pH 7.4 50 mL-1M Tris
100 mM NaCl
5% FBS
25 mL 0.02% Sodium Azide
100 ul—Mouse and Rabbit IgG
Bring volume up to 1 L with distilled water Results
Induction of mismatch repair pathway in cells. When a mismatch occurs due to O4-methylguanine adduct (chemical or environmentally induced), MMR complexes (MutS and MutL) translocate to the nucleus, recruit repair signals and initiate further repair or cell death (FIG. 1; Mirzoeva et al., *Mol Cancer Ther.*, 5:2757-66 (2006); Eich et al., *Mol Pharmacol.*, 78:943-51 (2010)). To develop an FVA test to assess defects in the mismatch repair pathway (MMR deficiency, also known as LS) and demonstrate the analytical and clinical validity of the test in a retrospective cohort that was collected by the National Cancer Institute's Colon Cancer Family Registry (CCFR). Patients in this CCFR cohort came from Mount Sinai Hospital/Samuel Lunenfeld (Toronto), Fred Hutchinson Cancer Research Center (Seattle) and Mayo Clinic CCFR (Phoenix). The cohort consisted of 180 individuals and separated into three groups: Group 1 has a known pathogenic variant in MMR genes: MLH1, MSH2, MSH6 and PMS2; Group 2 have significant family histories and no pathogenic variants in MMR genes as determined by ClinVar, but do have either high MSI and/or loss of MMR proteins (measured by immunohistochemistry) in tumors; and Group 3 are family members of known carriers of pathogenic variants in MMR genes who themselves do not carry the variant. In development of this test a subset of Group 1 and Group 3 LCLs from CCFR were treated with MNNG. First, to determine a concentration of MNNG that doesn't induce cell death a dose response was conducted and cell survival was determined by trypan blue staining. MNNG concentrations 50 µM or less for 24 hours did not significantly increase cell death compared to untreated control in Group 3 (FIG. 2A; n=3). Next, using dose response of MNNG on Group 1 and Group 3 LCLs, risk scores were measured (developed from combining FVAs of MLH1, MSH2 and ATR). Comparing Group 1 and 3, 50-25 µM of MNNG had a significant difference in risk score between the two groups (FIG. 2B, $p<0.01$, n=3 samples per group). Finally, Diazald® was used as a potential alternative to MNNG, and in comparison, between the two mismatch-inducing agents, Diazald® provided similar risk classification scores as MNNG on the same set of cells (FIG. 2C, $r^2=0.98$, n=3 per group). A concentration of about 50 µM MNNG was identified as the optimal concentration for MMR induction.

Figure 4A:
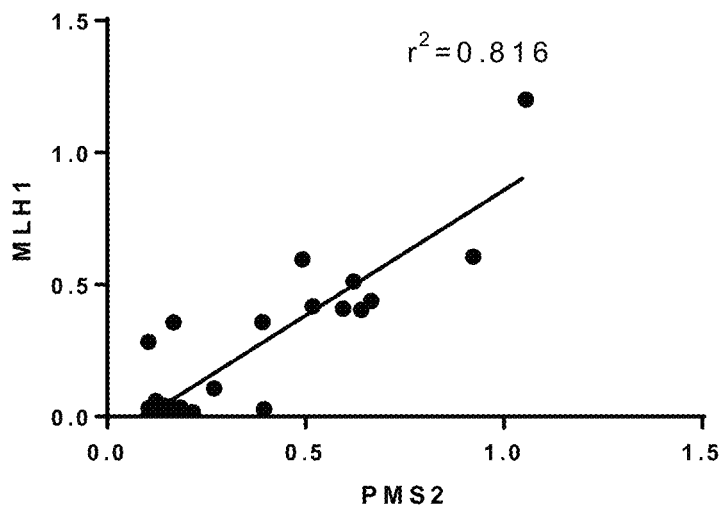
FIG. 4A-4C show correlation of assays. To determine if there was overlap between FVA assays, the same LCLs were compared between assays.
Figure 4B:
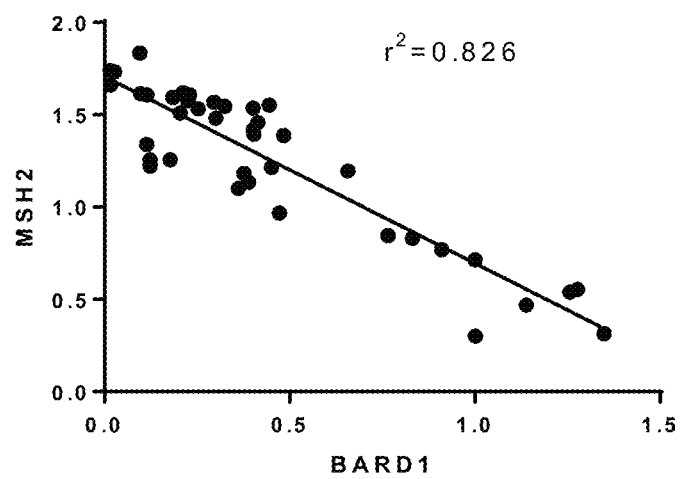
Figure 4C:
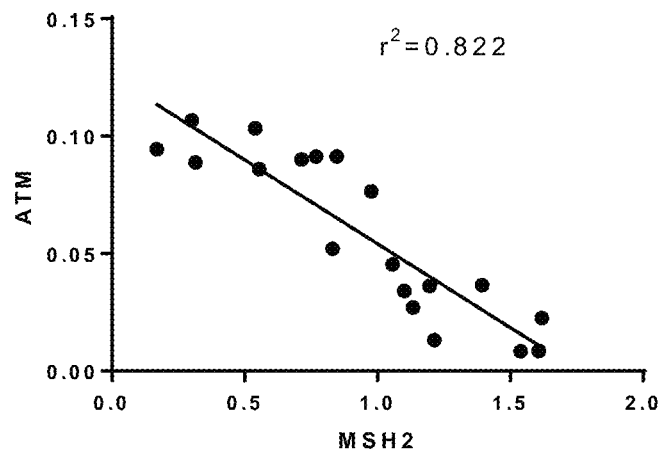
Figure 5A:
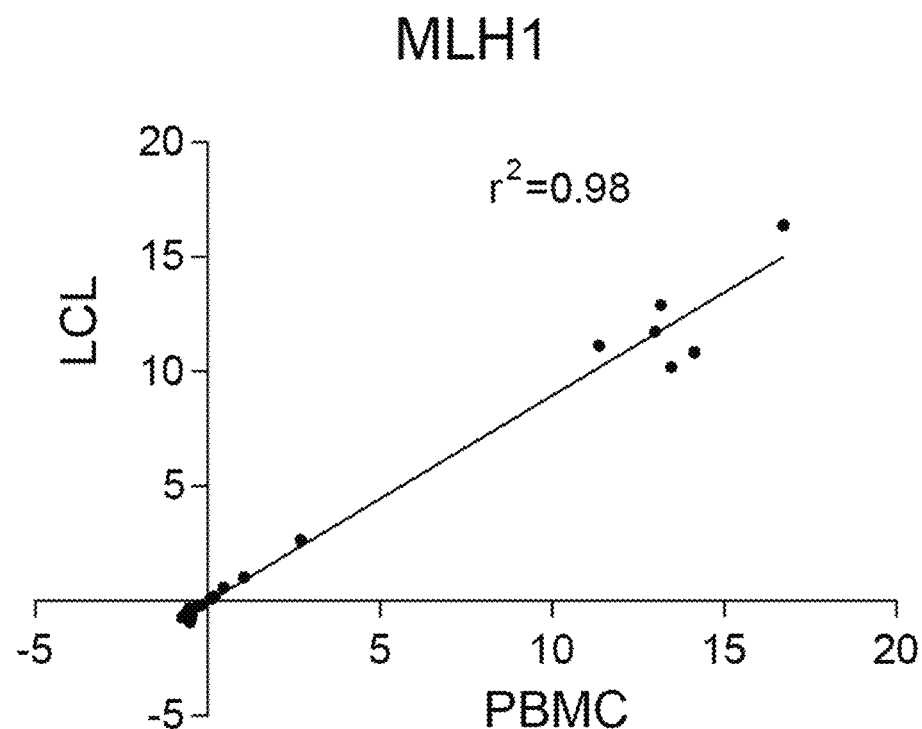
FIG. 5A-5D show correlation of assays in multiple cell types (transformed LCL and PBMC). 20 PBMC samples and their derived LCLs were used to compare if results are correlated between LCLs and PBMCs. Ten samples were from Group 1 and ten from Group 3. Using linear regression, the 3 assays have an $r^2$>0.85, high correlation.
Figure 5B:
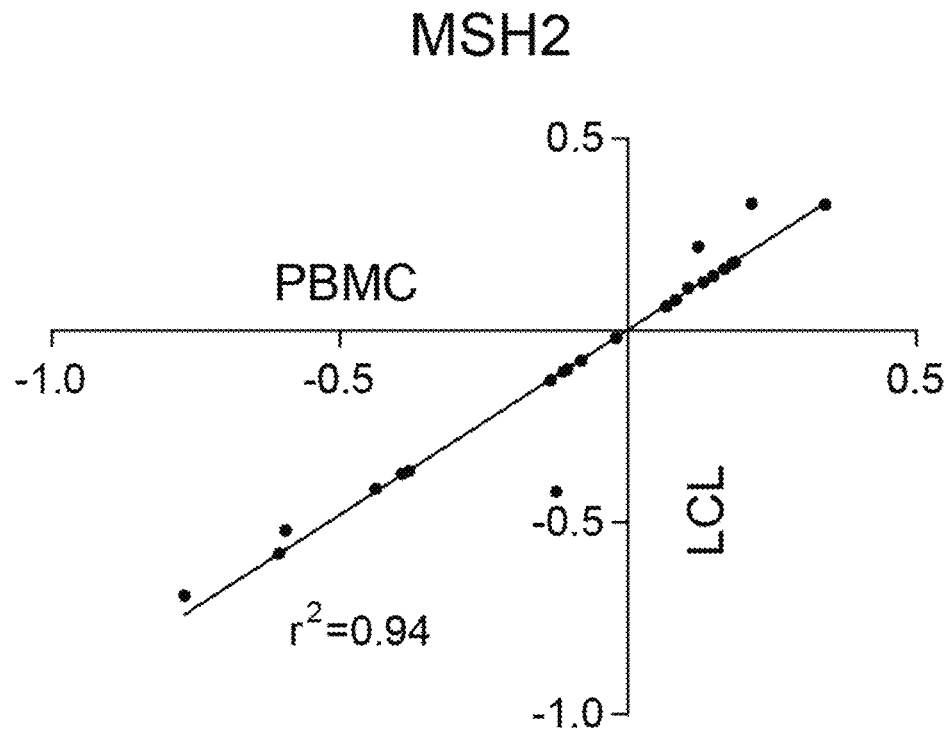
Figure 5C:
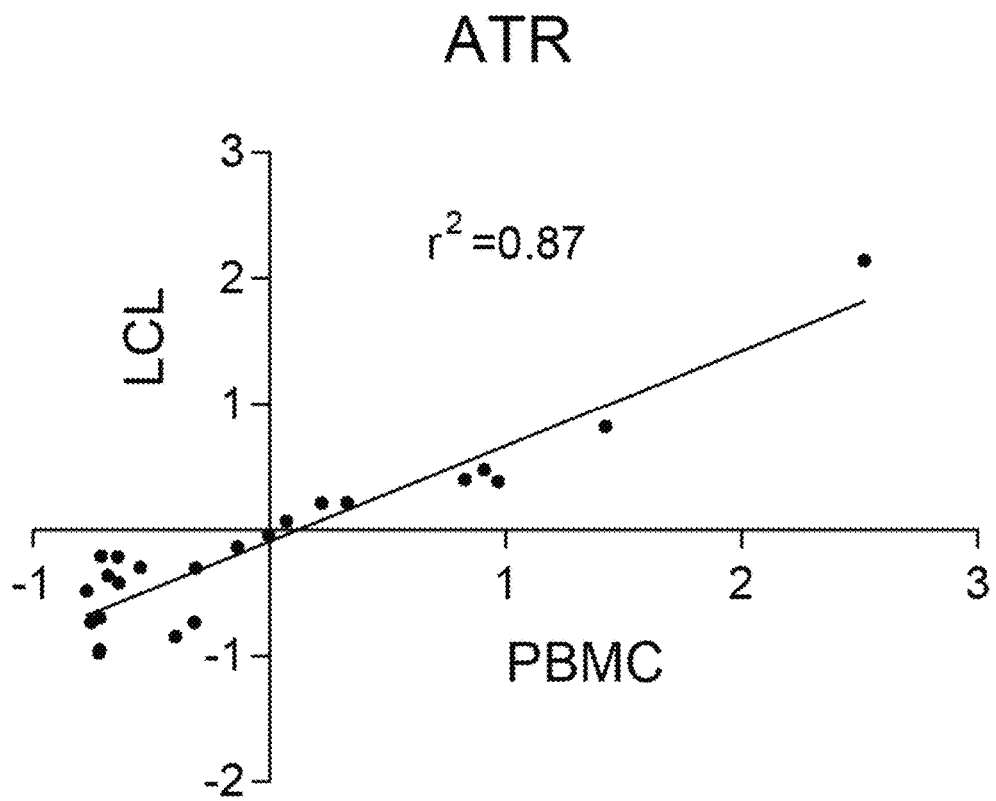
Figure 5D:
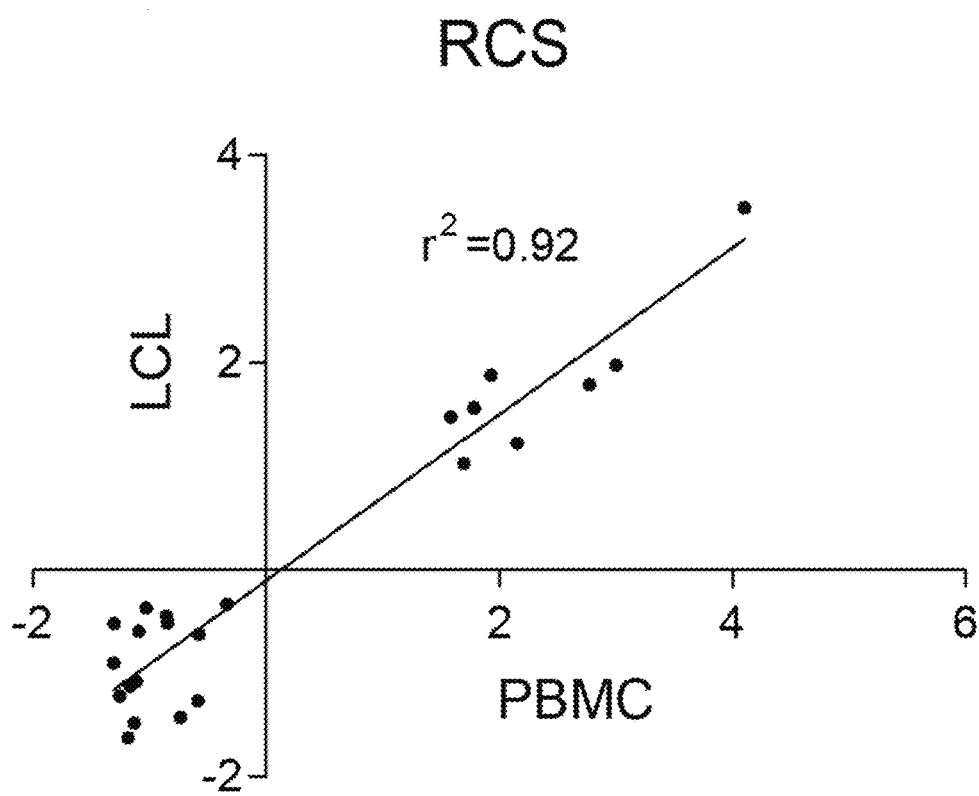

Identifying variables and establishing risk classification scores for LS. In the FVA assay developed for the assessment of DSB repair pathway, a number of critical points were identified and used for the development of their risk classification score (Syeda et al., *Genet Med.*, 19(9)1071-7 (2017)). As LS does not arise from deficiencies in the DSB pathway, novel critical points needed to be identified in the MMR pathway. FVA assays were developed for MLH1, BARD1, PMS2 and MSH2 nuclear localization, and phosphorylation of ATR and ATM. When comparing LCL cells from Group 1 to Group 3, all assays had significant differences between the two groups (FIG. 3A-F, n=20 per group). While all tests show significant differences between the two groups, most tests have an accuracy (weighted specificity and sensitivity)<90%. In order to develop a >95% accuracy, FVA assays need to be combined to develop a risk classification score (see Table 1). Prior to the development of the risk classification scores, each individual assay was compared to each other to identify redundant assays. PMS2 and MLH1; MSH2 and BARD1; and ATM and MSH2 had high correlated FVAs (FIG. 4 A-C; $r^2>0.8$). In the building of risk classification scores these paired FVA assays can be interchanged and suggest inter dependency on each other in MMR. Logistic regression of FVAs of MLH1 and MSH2 nuclear localization and ATR phosphorylation identified coefficients for each assay. Using these coefficients, a risk classification score was given to each individual in Group 1, 2 and 3 (FIG. 3I-L; n=60 samples per group). The sensitivity was 100% and specificity was 98% of the combined FVA assays and an accuracy (weighted mean of sensitivity and specificity) was 99% (see Table 1).

TABLE 1

MMR FVA specificity, sensitivity and accuracy.

| Test | Sensitivity | Specificity | Accuracy |
| --- | --- | --- | --- |
| MLH1 FVA | 65% | 90% | 78% |
| MSH2 FVA | 75% | 75% | 75% |
| ATR FVA | 95% | 95% | 95% |
| RCS Discovery Cohort | 100% | 95% | 98% |
| RCS Replication Cohort | 100% | 98% | 99% |

Transitioning from LCL to PBMC. While LCLs are useful in a research setting, the transformation of LCLs for the purposes of a clinical diagnostic is time consuming and expensive. DSB repair FVAs have previously shown robust sensitivity and specificity using PBMCs (Syeda et al., *Genet Med.*, 19(9)1071-7 (2017)). Transitioning from LCL cells to PBMCs was done by taking a small cohort of 20 individuals (10 Group 1 and 10 Group 3) collected from patients at the Montefiore Medical Center Cancer Genetics Service. The PBMCs were isolated, half of each sample were processed for MMR FVA and the other half were transformed for LCLs, which were also processed for FVA after transformation. To demonstrate reproducibility between LCL and PBMCs, we compared the FVA results from 3 assays between the cell types and observed a >0.9 $r^2$ by linear regression (FIG. 5 A-D; MLH1 FVA had $r^2$=0.98, MLH2 FVA had $r^2$=0.94 and ATR FVA had $r^2$=0.87). Replicates of the PBMC samples had CVs less than 5% (MLH1 CV=1.29%, MSH2 CV=1.49% and ATR CV=2.36%). Patient samples were stored at room temperature or lower and PBMCs were isolated within 72 hours of blood draw. Colder temperatures (<15° C.) and longer times from blood draw (>72 h) result in poor PBMC yields (less than 10,000 cells/ml).

Figure 6A:
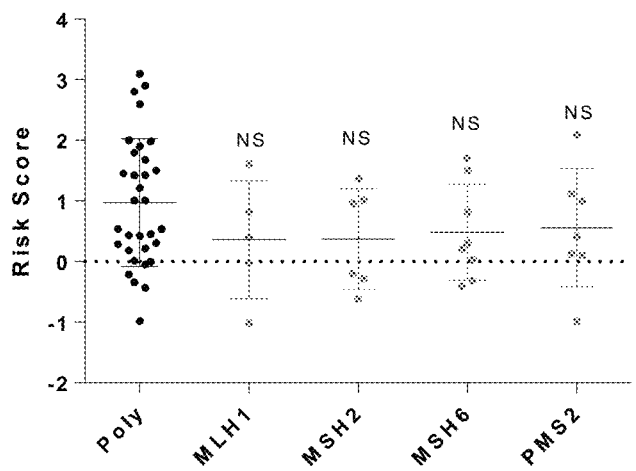
FIG. 6A-6C show Group 2 analysis by VUS location and comparison with Group 1 and Group 3. LCL cells from individuals in group 2 had a VUS in MMR genes.
Figure 6B:
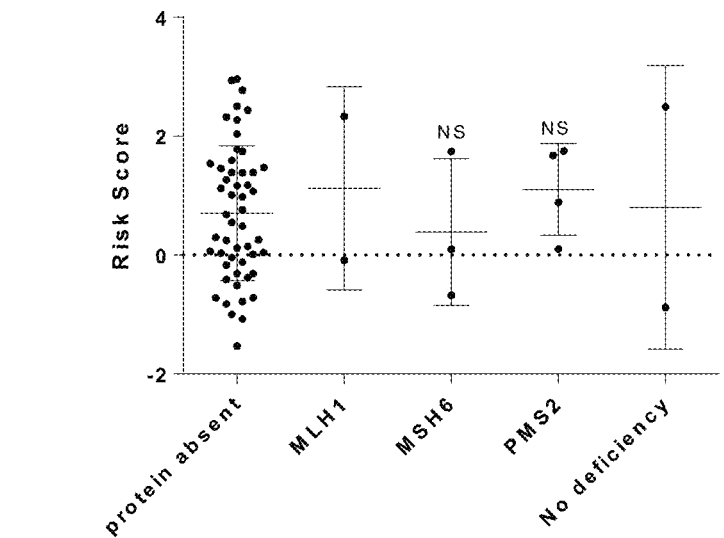
Figure 6C:
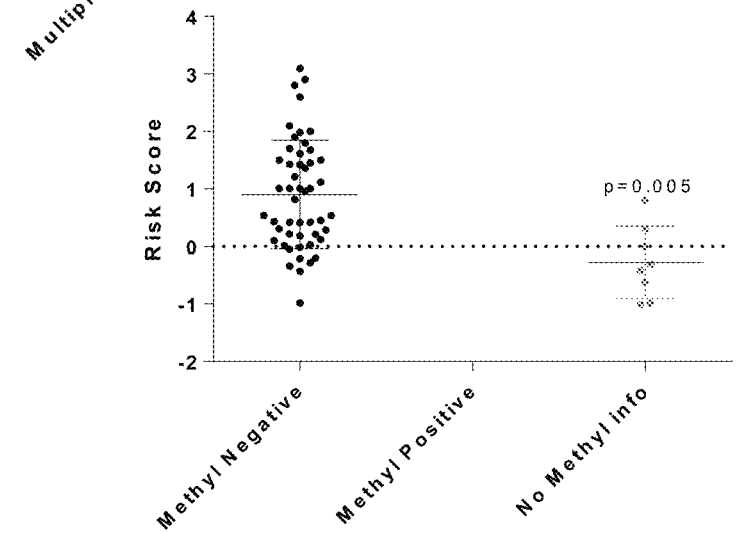
Figure 7A:
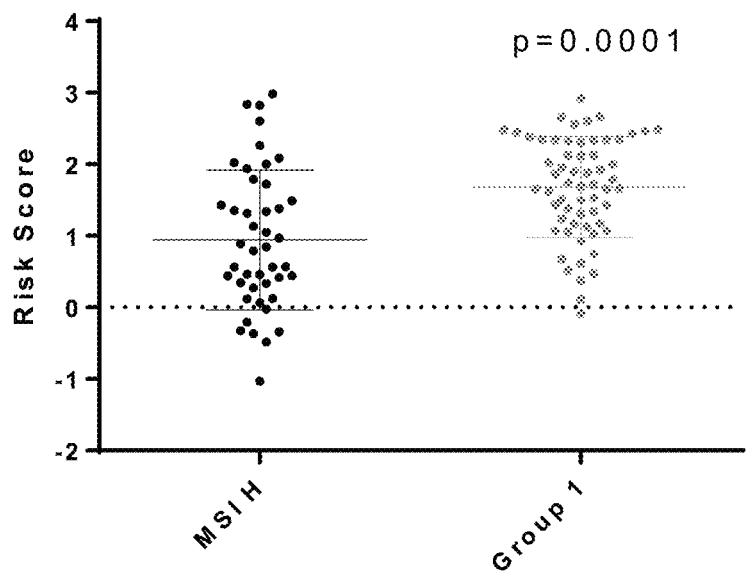
FIG. 7A-7B compare Group 2 MSI-H with Groups 1 and 3. MSI is a criterion in the Bethesda guidelines for defining LS. In group 2, which contains VUS, MSI-H samples were plotted and compared to Group 1 (individuals with pathogenic MMR mutation) and Group 3 (individuals not carrying known familial pathogenic pathogenic variants).
Figure 7B:
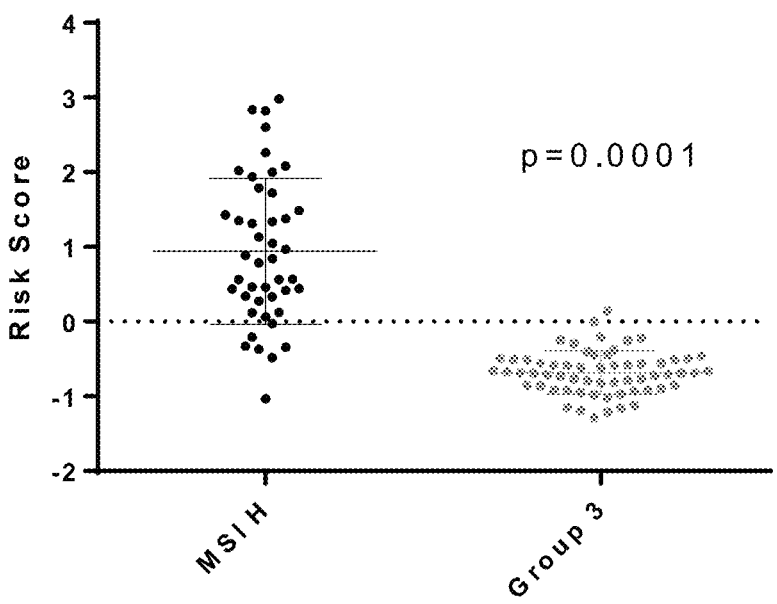

Majority of patients with MSI-H and VUS reclassified as high-risk using FVA. While panel sequencing can identify pathogenic and benign variants, there remains a 20-40% of at-risk LS patients who have VUS (Moriera et al., *JAMA*, 308(15) 1555-65 (2012)). Group 2 in the CCFR cohort have VUS in either MLH1, MSH2, MSH6, PMS2 or in 75% of patients in multiple genes (FIG. 6A). Immunohistochemistry of tumors from group 2 had absence of MLH1, MSH2, MSH6, PMS2 and in 85% of subjects multiple MMR proteins (FIG. 6B). To exclude possibility that tumors in group 2 may be from MLH1 methylation (as opposed to MMR gene variant), MLH1 promoter methylation was measured, 88% had no methylation with the remaining 12% either having no methylation information or failed tests (FIG. 6C). In the clinic, patients with uncertainty often have to wait until they develop tumors, at which point they are diagnosed with LS using MSI PCR testing and the revised Bethesda criteria (Parsons et al., *Cancer Res.* 55:5548-50, (1995); Lindor et al., *J Clin Oncol.* 20(4):1043-8 (2002)). Of the samples that were identified as MSI-H in group 2, 89% had a high-risk classification score when tested with FVA, similar to group 1, although different means (FIG. 7A n=53). The group 2 MSI-H were significantly different than group 3 (FIG. 7B). Those individuals with MSI-H tumors but benign FVA results, may have had somatic pathogenic variants resulting in MSI-H.

Figure 8A:
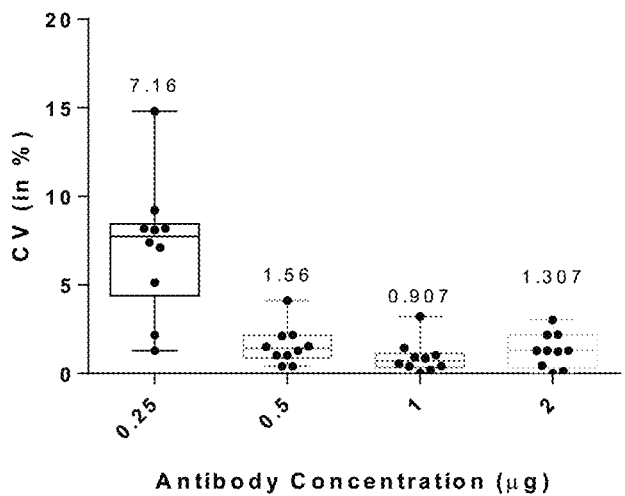
FIG. 8A-8C show that reproducibility of assays is enhanced under certain conditions. Reproducibility of the assay was measured.
Figure 8B:
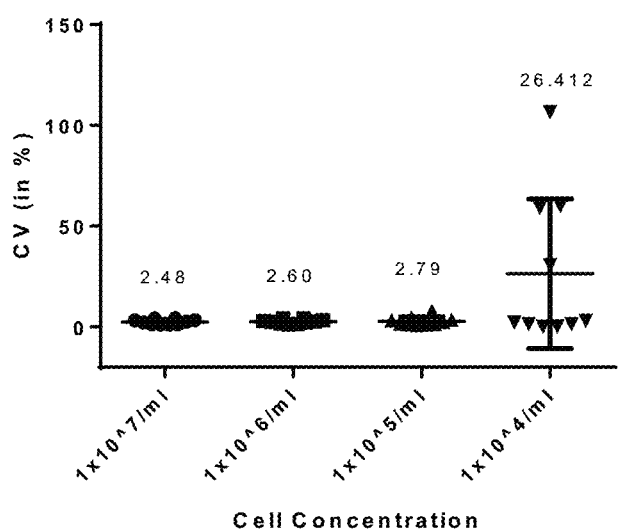
Figure 8C:
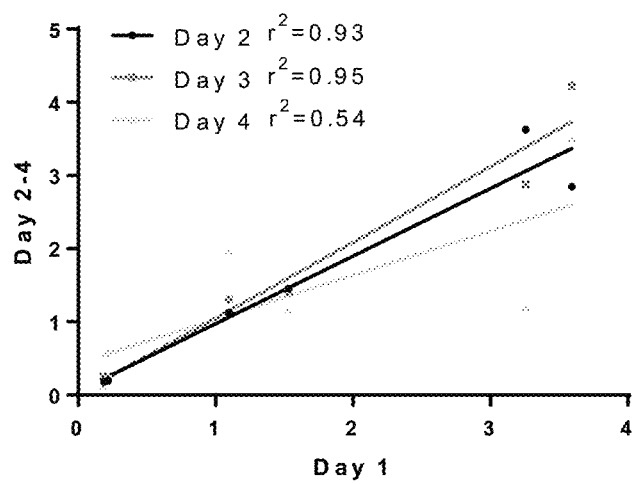

Stability of FVA assays. The optimal concentration of antibodies and cell number in each assay was determined by using respective dose curves and comparing CVs from 3 technical replicates. The assays require a minimum antibody concentration of 0.5 μg (FIG. 8A, CV=1.56%) and a minimum cell concentration of 1×10^5 cells/ml (FIG. 8B, CV=2.79%). Flow cytometry and FVA results reported in this study were done within 24 hours of staining. However, to determine if staining is stable over multiple days, stained cells stored at 4° C. had their CV compared for each 24 hours from staining on Day 1 (FIG. 8C). Staining is stable for up to 3 days in 20 LCL cell lines from CCFR (consisting of both Group 1 and Group 3; risk score CVs are Day 2 $r^2$=0.93, Day 3 $r^2$=0.95, Day 4 $r^2$=0.54). If there is a delay between staining and cytometry, this kit is stable for up to 72 hours.

Figure 9A:
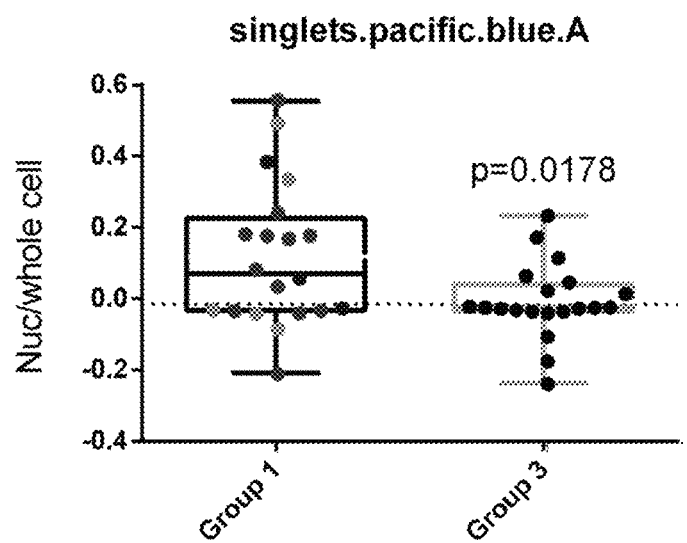
FIG. 9A-9C show cellular phenotype and optical differences occur in LS cell lines, compared to non-LS. Using raw data from the flow cytometry machine we were able to determine that in addition to MMR pathway changes there were morphological changes in the cells between Group 1 and Group 3. Specifically changes in brightness of nuclear stain (FIG. 9A), changes in size (FIG. 9B) and changes in complexity (FIG. 9C).
Figure 9B:
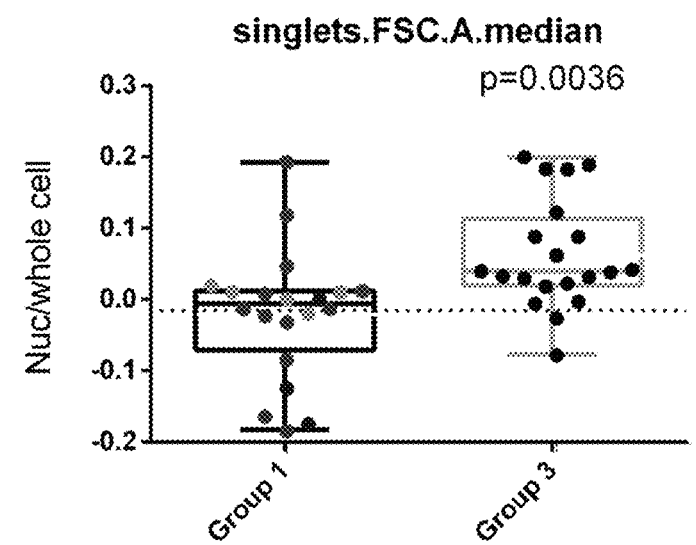
Figure 9C:
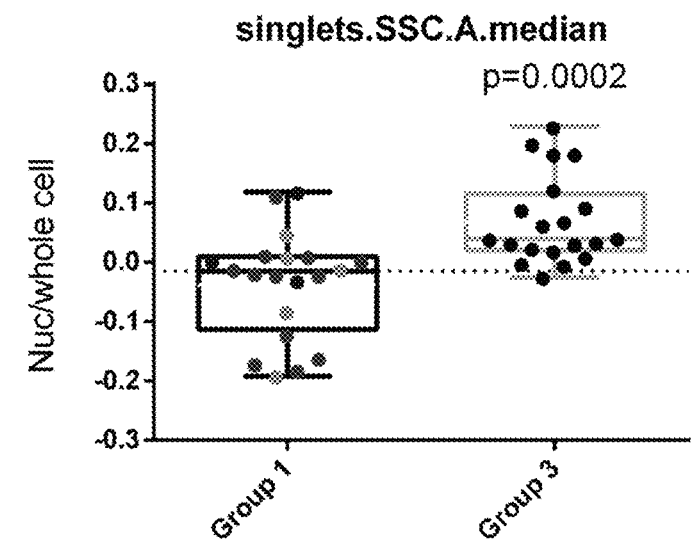
Figure 10:
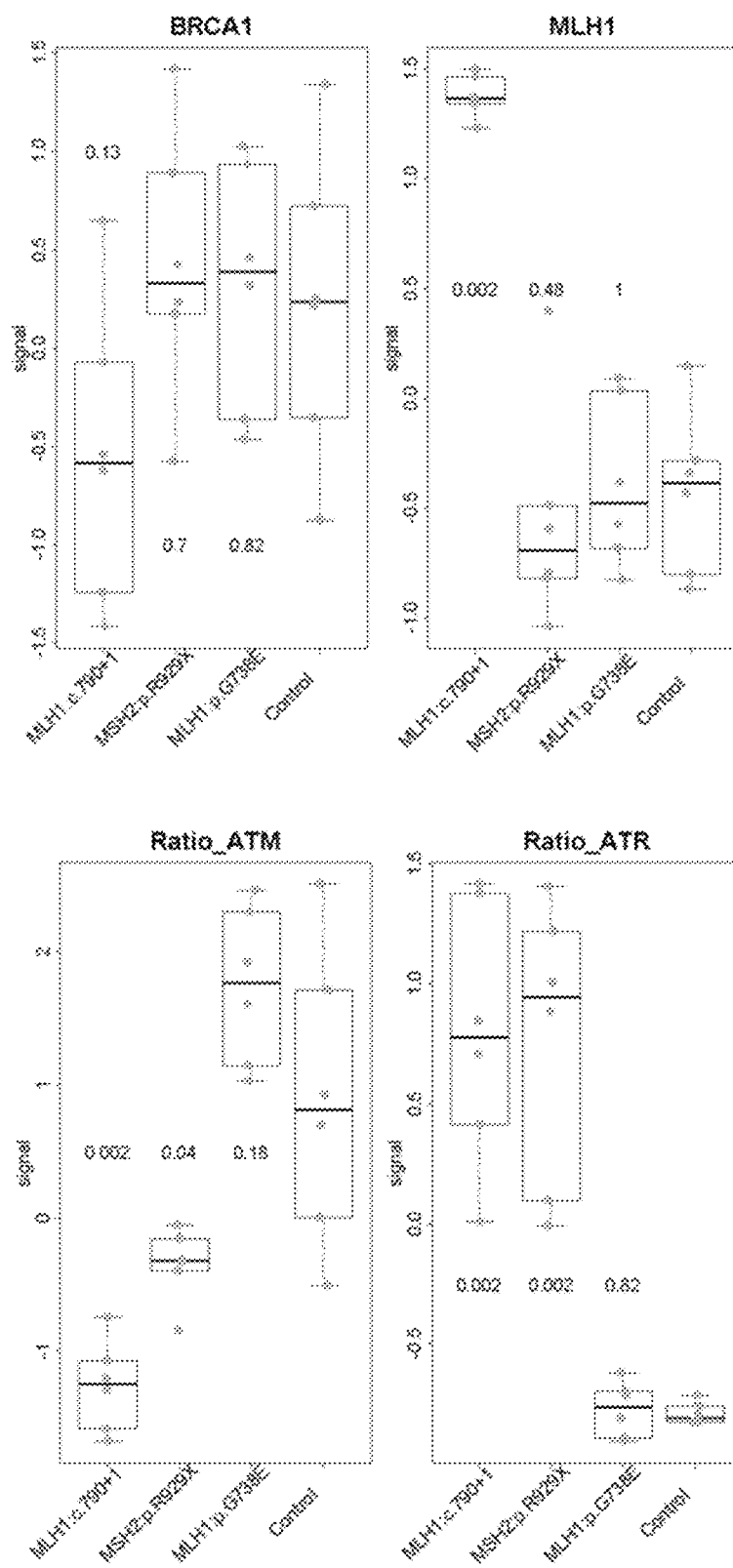
FIG. 10 shows pathogenic variants and VUS in edited cell lines affect response to MNNG treatment as detected by FVAs. Boxplots compare standardized nuclear localization of MLH1 and phosphorylation of ATM and ATR expressed in ratios of phospho/total protein. P-values of the pairwise comparisons of the variants relative to control by the Mann-Whitney test are shown.

FVA can detect morphological differences between cells with pathogenic and benign variants. In addition to the MMR protein targets, changes in morphology and DNA staining between Group 1 and Group 3 after inducing MMR was also investigated. In order to do this raw data from BD DIVA software was exported and different parameters were compared. Group 1 had significantly higher intensity of DAPI staining compared to Group 3 (FIG. 9A, n=20 per group). Forward-scatter of light is used in the size of nuclei and whole cell, group 1 have significantly smaller nuclei than group 3 following MMR-induction (FIG. 9B; n=20 per group). Side-scatter of light can be used to determine internal complexity, and Group 1 have significantly lower complexity than group 3 in the nuclei (FIG. 9C; n=20 per group). This provides the possibility that in addition to MMR targets, FVAs can be developed for cellular complexity, size and DNA staining intensity as additional variables for determining risk classification and diagnosing LS.

Figure 11:
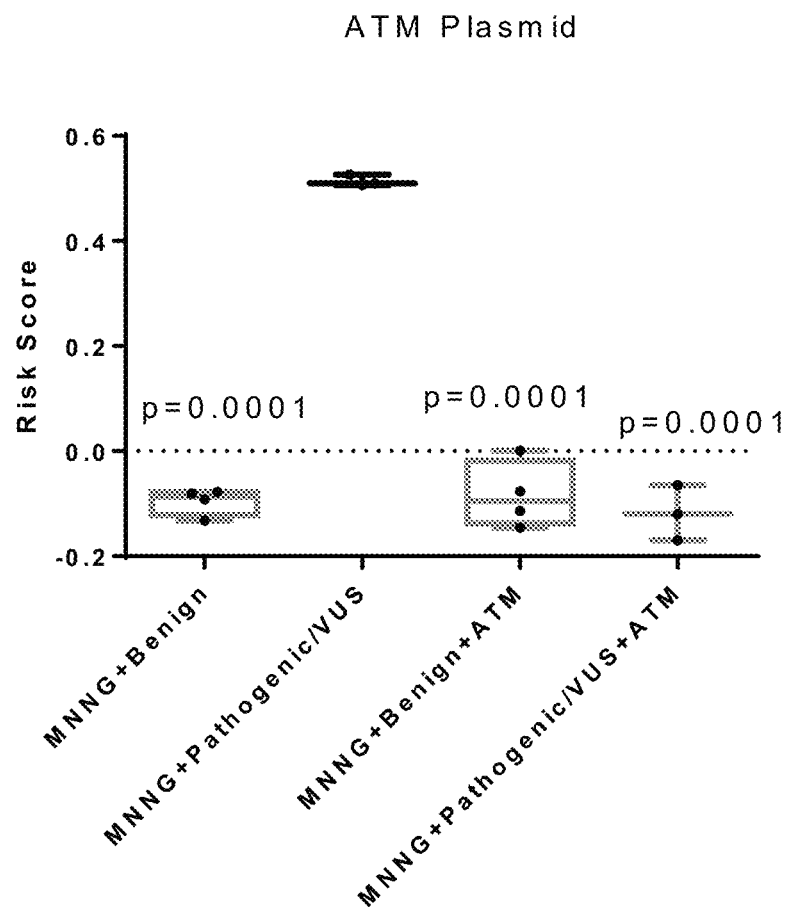
FIG. 11 shows ATM pathogenic variants are rescued by transfection with wild-type ATM plasmid. LCL cells from patients with ATM pathogenic variant and those with benign variants are transfected with wild-type ATM plasmid. Transfection of wild-type ATM plasmid in cells with pathogenic ATM restored MMR FVA to a benign risk classification score. Transfection of wild-type ATM plasmid did not significantly change FVAs for cells with benign variants.
Figure 12A:
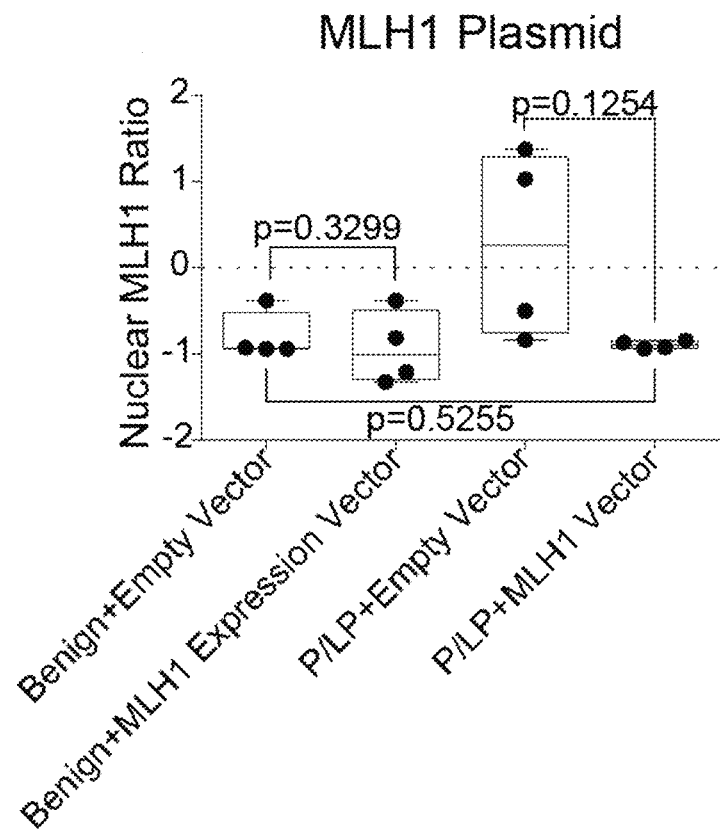
FIG. 12A-12H show transfection of wild-type cDNA expression plasmid restores benign FVA results in edited cells with P/LP variants. Boxplots of CRISPR/Cas9 edited cells with either benign or P/LP variants in MLH1 (n=4 each) or MSH2 (n=4 each) and transfected with empty vector or wild-type expression plasmid containing cDNA of the corresponding edited variant.
Figure 12B:
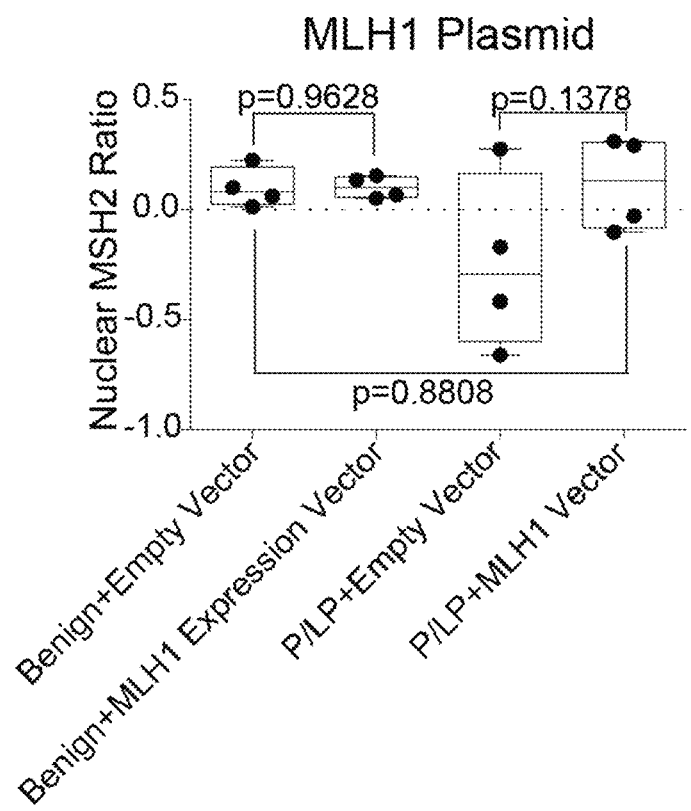
Figure 12C:
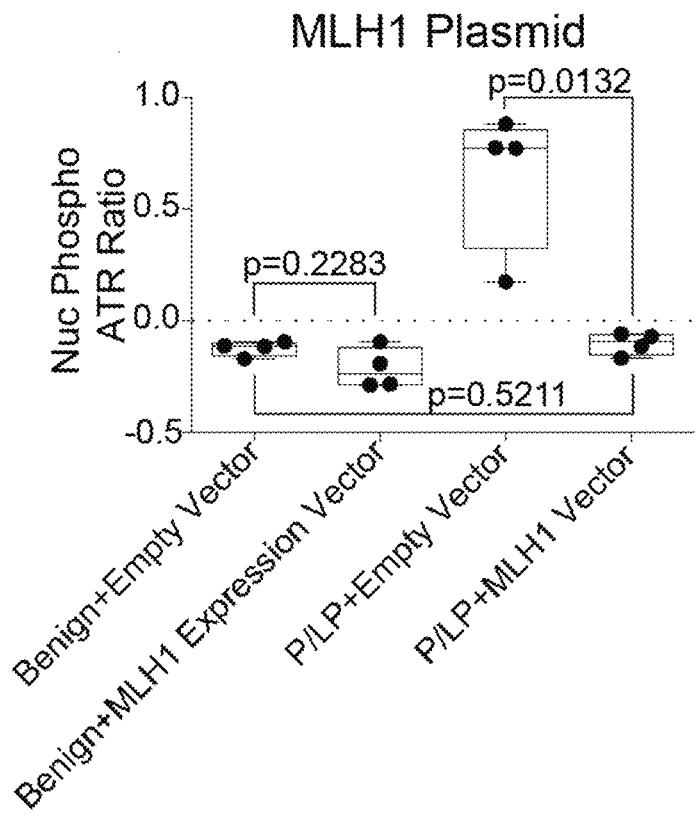
Figure 12D:
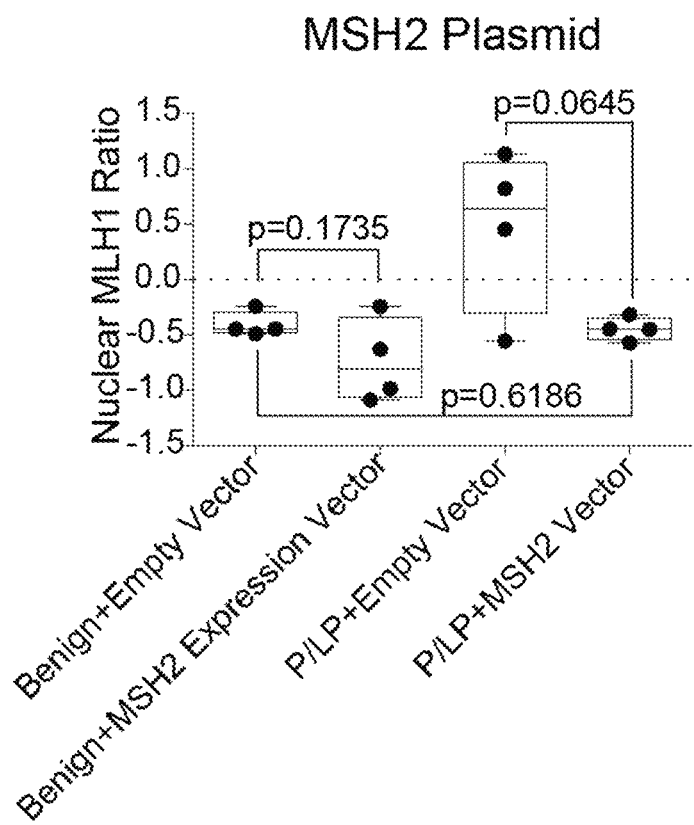
Figure 12E:
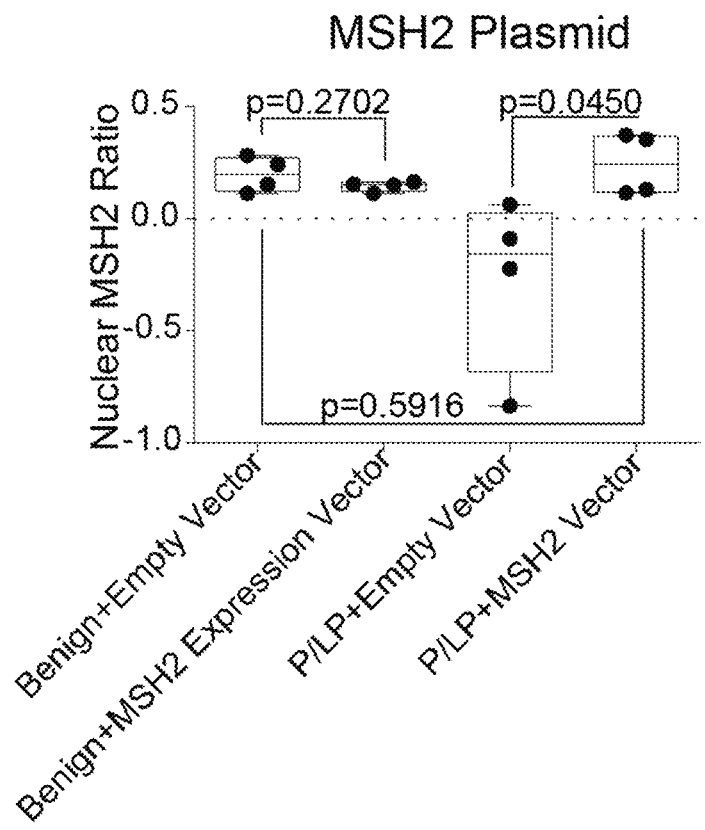
Figure 12F:
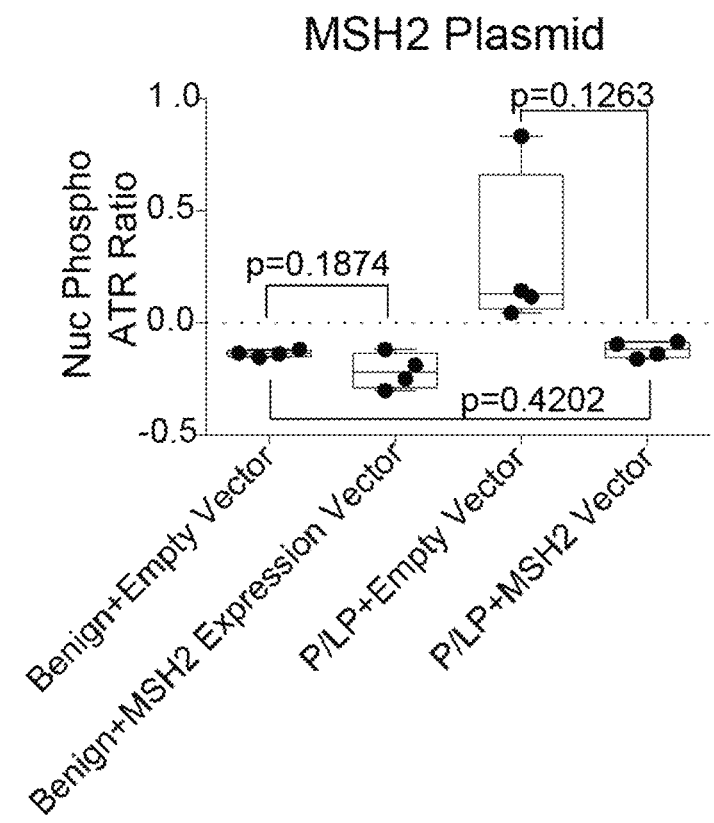
Figure 12G:
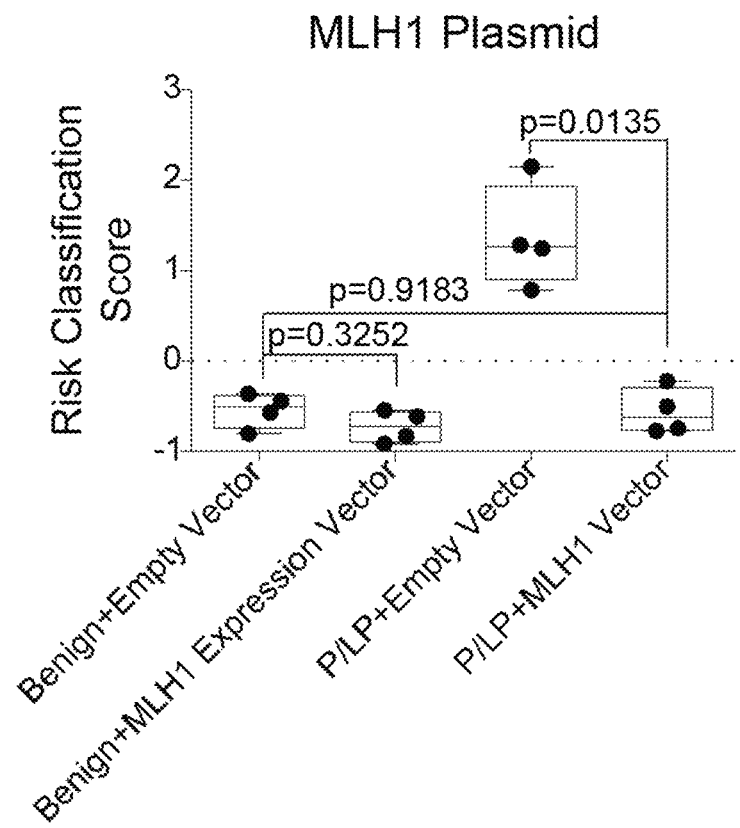
Figure 12H:
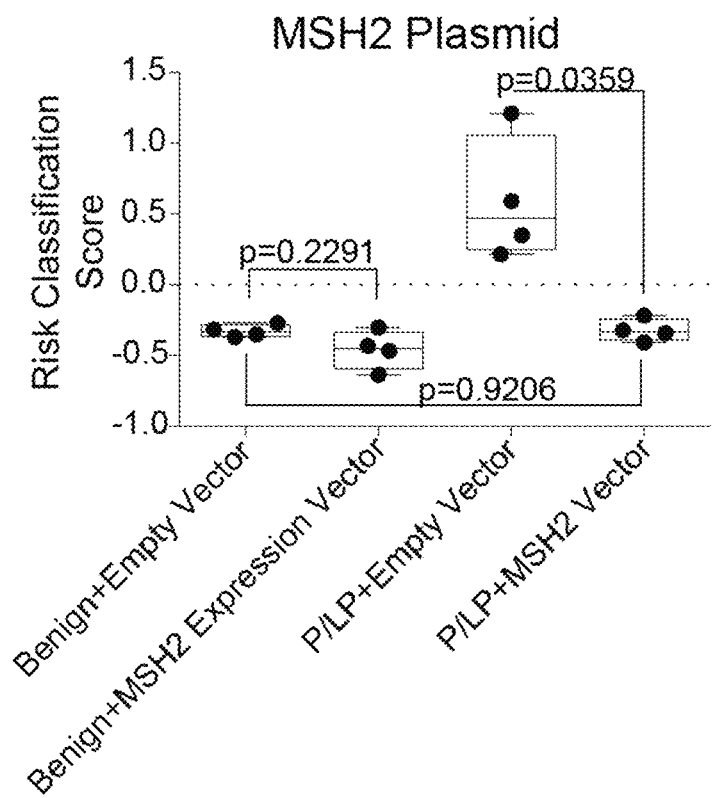
Figure 13A:
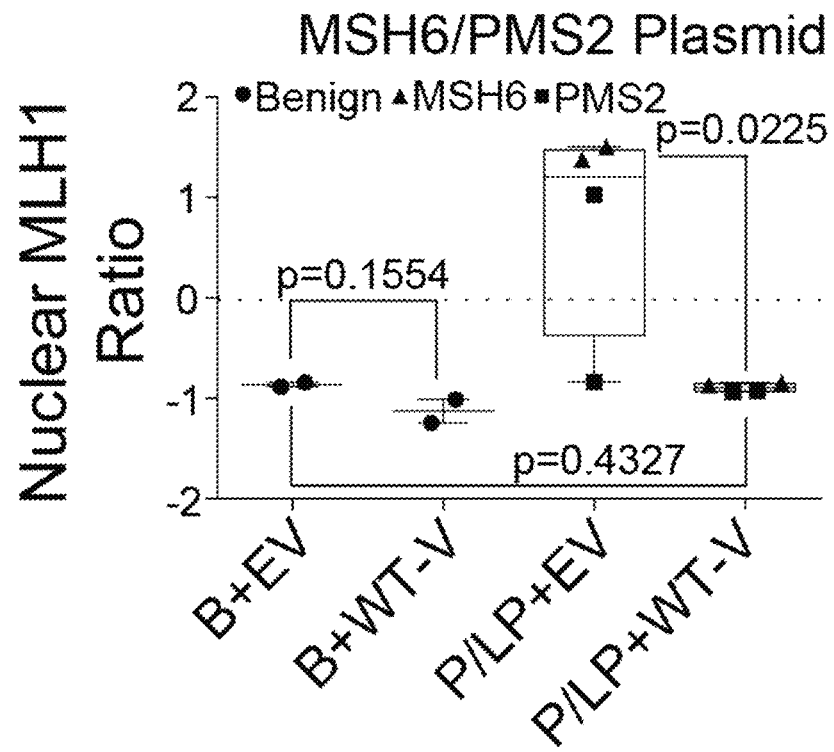
FIG. 13A-13D show transfection of corresponding wild-type cDNA expression plasmid restores benign FVA results in edited cells with MSH6 and PMS2 P/LP variants. Edited HEK293 cells with benign (B+; circles) or P/LP variants in MSH6 (2 variants; triangles) or PMS2 (2 variants; squares) transfected with either empty vector (EV) or corresponding WT cDNA expression vector (WT-V).
Figure 13B:
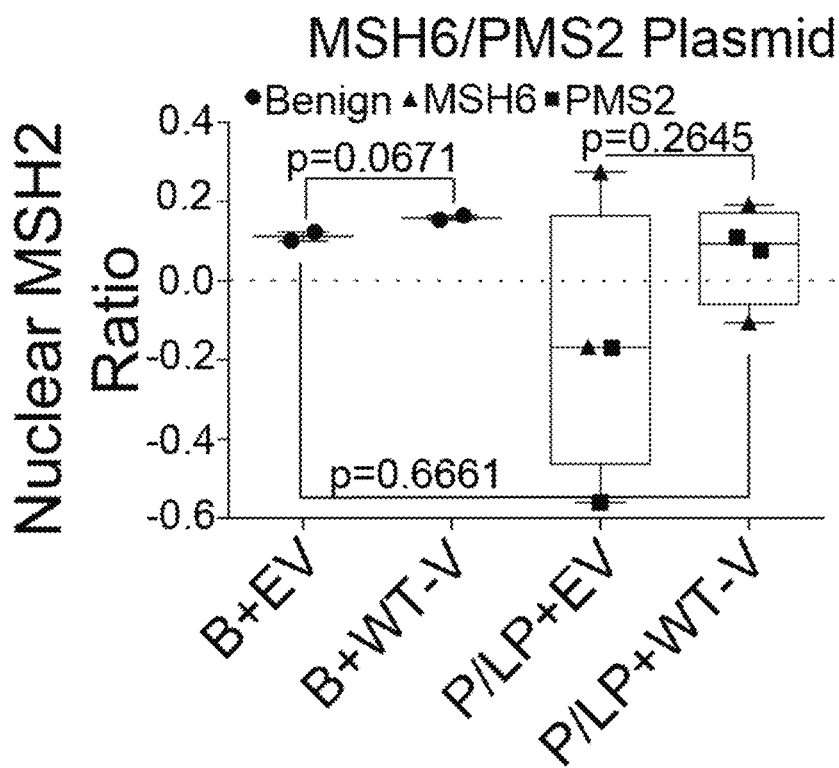
Figure 13C:
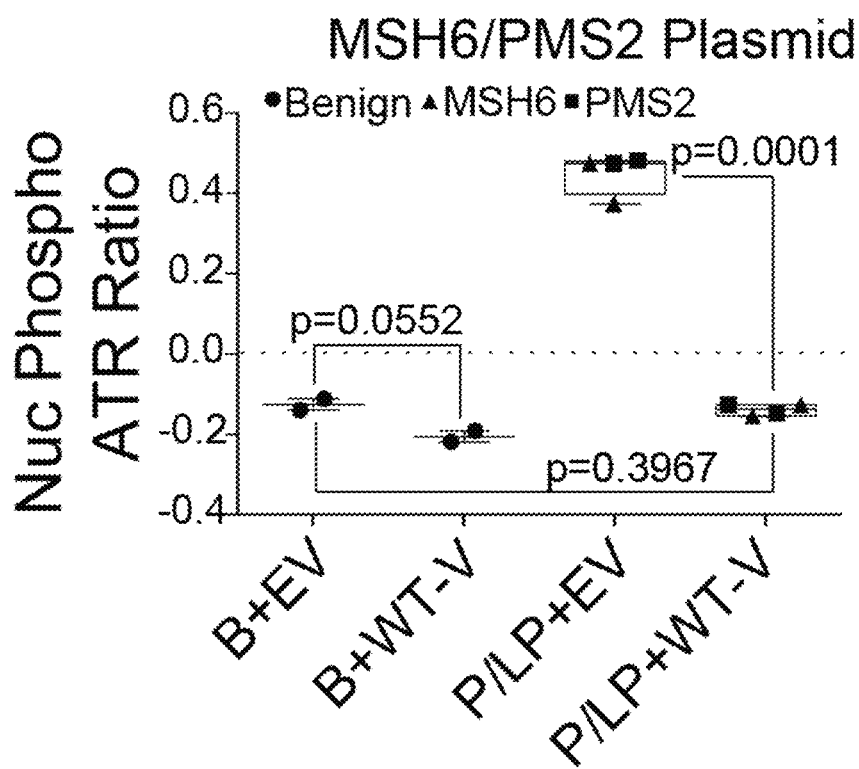
Figure 13D:
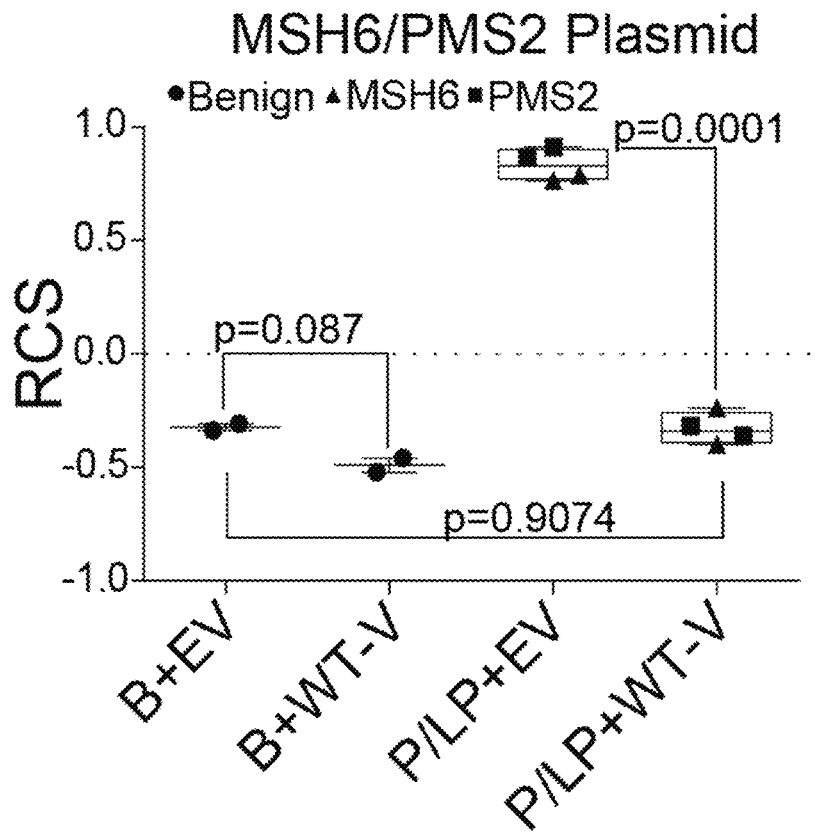

Using FVA to validate annotation of variants. While FVAs are useful in annotating patient samples in real time, many of these VUS need to be validated and in some cases when patient samples are not available, but VUS is known, FVA on MMR targets can be used. In these models, CRISPR-Cas is used to edit DNA of LCL cells with known pathogenic, benign and uncertain significance variants. FVAs for MLH1 and MSH2 nuclear localization and ATR phosphorylation show differing phenotypes between pathogenic and benign variants, and validate their annotation (FIG. 11, 12, 13). These pathogenic FVA phenotypes can be rescued by transfection with wild type cDNA expression plasmids. While this may appear to be similar to cell based models, there are certain critical differences: 1) FVAs use multiple assay targets (>3) while many cell based models use a single target and 2) the use of human LCLs differ from yeast models that are used (Takahashi et al., *Cancer Res.* 67:4595-04 (2007); Maresca et al., *Front Gent.*, 10.3389 (2018)). Validating of these pathogenic variants can be done through rescue experiments, where CRISPR modified genes or LCLs from patients with known variants have a wild type gene introduced which determines if the variant was necessary in the disruption of the MMR pathway. Pathogenic variants in MLH1, MSH2, MSH6, PMS2 or ATM show a pathogenic risk classification score in MMR FVAs. Rescuing these cells by transfection of wild-type cDNA expression plasmids changes risk classification score to benign (FIG. 11-13). This rescue from pathogenic to benign risk classification score confirm that the variants are causal for MMR deficiencies.

DISCUSSION

This disclosure provides a novel method of using FVA technology to probe the MMR pathway and develop a test to diagnose LS. FVA assays in MLH1, MSH2, BARD1 and PMS2 nuclear localization; and ATM and ATR nuclear phosphorylation show significant difference when comparing LCL cells with pathogenic variants (Group 1) versus family members of pathogenic variant carriers without variants (Group 3). Combining the FVA assays of MLH1, MSH2 and ATR a risk classification score was developed with a sensitivity of 98% and specificity of 95%. Applying this score to patients with VUS in MMR genes (Group 2) 73% were reclassified as having germline MMR deficiencies and 27% not having germline MMR deficiencies. MMR FVA assays were successfully transitioned to PBMC, providing a rapid and inexpensive clinical assay that can accurately annotate MMR variants and diagnose LS.

Diagnosing LS using Amsterdam II criteria and panel sequencing accurately diagnoses 60-80% of patients as either having pathogenic or benign variants (Moriera et al., *JAMA*, 308(15) 1555-65 (2012)). The remaining individuals with VUS are diagnosed with LS using MSI testing and revised Bethesda criteria (Umar et al., *J Natl Cancer Inst.*, 96(4)261-268 (2004)). MSI testing is: invasive, can only be done on already formed tumors (after person has developed cancer) and can detect somatic cancers in addition to germline (Parsons et al., *Cancer Res.* 55:5548-50, (1995); Lindor et al., *J Clin Oncol.* 20(4):1043-8 (2002); Sourrouille et al., *Fam Cancer*, 12(1): 27-33 (2013)). The FVA assay developed here to diagnose LS requires a blood sample, can be done on individuals without known cancers and have 98% accuracy when diagnosing known pathogenic and benign variants, and reannotating 73% of individuals with VUS and/or MSI-H. Other molecular models used to annotate variants, such as CIMRA and yeast/cell-based assays are time consuming, and does not use original patient cells (Drost et al., *Genet Med.*, 21(7):1486-96 (2019); Drost et al. *Gent Med.*, 847-56 (2020)). MMR FVA assays can use PBMCs, providing the opportunity for this assay to be used in a clinical setting.

The targets and pathways are distinct to prior FVAs which focused on diagnosing HBOC and 46,XY gonadal dysgenesis (Loke et al. *Clin Genet.*, 81(3): 272-7, (2012); (Loke et al. *Hum Mol Genet.*, 24:3030-7 (2015)). The methods disclosed herein were developed to complement LS, and reclassify individuals with a VUS and unknown tumor status in a direct manner. While this test is targeted towards classifying individuals with VUS, it has the potential to be an alternative to panel sequencing when diagnosing LS.

Having described the disclosure in detail and by reference to specific embodiments thereof, it will be apparent that modifications and variations are possible without departing from the scope of the claimed subject matter. More specifically, although some aspects of the present disclosure are identified herein as particularly advantageous, it is contemplated that the present disclosure is not necessarily limited to these particular aspects of the disclosure.

The invention claimed is:

1. A method for screening a population of cells from a human subject for functionality of the mismatch repair (MMR) pathway, the method comprising:
    (a) contacting the population of cells with a DNA mismatch-inducing agent;
    (b) measuring via flow-cytometry in the population of cells at least one functional activity of the mismatch repair (MMR) pathway, wherein the at least one functional activity comprises nuclear localization of mutL homologue 1 (MLH1) and mutS homologue 2 (MSH2);
    (c) comparing the nuclear localization of MLH1 and MSH2 in the population of cells contacted with the DNA mismatch-inducing agent with the nuclear localization of MLH1 and MSH2 from a control population of cells treated with the DNA mismatch-inducing agent and having a normal functioning MMR pathway; and
    (d) categorizing the MMR pathway as having loss of function or as having a partial-loss of function, based on the comparing step (c);
    wherein having loss of function or partial-loss of function of the MMR pathway indicates the subject as having Lynch Syndrome and one or more preventative interventions selected from colonoscopy, chemotherapy, chemoprevention, radiotherapy, immunotherapy, gene therapy, or surgery is administered to the subject having Lynch Syndrome.

2. The method of claim 1, wherein the population of cells comprises an introduced genetic variant or an expression plasmid.

3. The method of claim 1, wherein the DNA mismatch inducing agent is selected from the group consisting of SN1 DNA alkylators, 8-oxoguanine, 6-thioguanine (6-TG), fluoropyrimidines, cisplatin, radiomimetic agents, radiation, and UV light.

4. The method of claim 3, wherein:
    (a) the SN1 DNA alkylators are selected from the group consisting of N-methyl-N'-nitro-N-nitrosoguanidine (MNNG), N-methyl-N-nitroso-p-toluenesulfonamide, methylnitrosourea (MNU), procarbazine, and temozolomide;
    (b) the fluoropyrimidines are selected from the group consisting of 5-fluorouracil (FU), and 5-fluoro-2'-deoxyuridine (FdU); and
    (c) the radiomimetic agents are selected from the group consisting of Diepoxybutane, Mitomycin C, and Bleomycin.

5. The method of claim 4, wherein the SN1 DNA alkylator is N-methyl-N'-nitro-N-nitrosoguanidine (MNNG), or N-methyl-N-nitroso-p-toluenesulfonamide, or both N-methyl-N'-nitro-N-nitrosoguanidine and N-methyl-N-nitroso-p-toluenesulfonamide.

6. The method of claim 1, wherein the at least one functional activity of the MMR pathway further comprises BRCA1 associated RING domain 1 (BARD1) nuclear localization, postmeiotic segregation increased 2 (PMS2) nuclear localization, BRCA2 DNA repair associated (BRCA2) nuclear localization, p53 phosphorylation, ATM serine/threonine kinase (ATM) phosphorylation, or ATR serine/threonine kinase (ATR) phosphorylation.

* * * * *